United States Patent
Meerpoel et al.

(10) Patent No.: US 7,642,378 B2
(45) Date of Patent: Jan. 5, 2010

(54) LIPID LOWERING BIPHENYLCARBOXAMIDES

(75) Inventors: Lieven Meerpoel, Beerse (BE); Marcel Viellevoye, Breda (NL)

(73) Assignee: Janssen Pharmaceutica NV, Beerse (BE)

( * ) Notice: Subject to any disclaimer, the term of this patent is extended or adjusted under 35 U.S.C. 154(b) by 1217 days.

(21) Appl. No.: 10/474,281

(22) PCT Filed: Mar. 27, 2002

(86) PCT No.: PCT/EP02/03491

§ 371 (c)(1),
(2), (4) Date: Oct. 2, 2003

(87) PCT Pub. No.: WO02/081460

PCT Pub. Date: Oct. 17, 2002

(65) Prior Publication Data

US 2008/0081813 A1    Apr. 3, 2008

(30) Foreign Application Priority Data

Apr. 6, 2001  (EP) .................. 01201270

(51) Int. Cl.
C07C 233/65  (2006.01)
(52) U.S. Cl. ................................... 564/184
(58) Field of Classification Search .............. 564/184
See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,602,023 A * | 7/1986 | Kiely et al. | 514/346 |
| 4,647,576 A | 3/1987 | Hoefle et al. | |
| 4,739,073 A | 4/1988 | Kathawala | |
| 5,041,432 A | 8/1991 | Gaylor et al. | |
| 5,064,856 A | 11/1991 | Garrity et al. | |
| 5,120,729 A | 6/1992 | Chabala et al. | |
| 5,510,379 A | 4/1996 | Lee et al. | |
| 5,512,548 A | 4/1996 | Kushwaha et al. | |
| 5,760,246 A | 6/1998 | Biller et al. | |
| 6,617,325 B1 | 9/2003 | Lehmann-Lintz et al. | |

FOREIGN PATENT DOCUMENTS

| | | |
|---|---|---|
| CA | 2091102 A1 | 9/1993 |
| EP | 0491226 B1 | 8/1996 |
| EP | 0645377 B1 | 8/1997 |
| EP | 0645378 B1 | 8/2000 |
| EP | 0567026 B1 | 3/2003 |
| WO | WO 96/10559 A1 | 4/1996 |
| WO | WO 96/26205 A1 | 8/1996 |
| WO | WO 96/26948 A1 | 9/1996 |
| WO | WO 96/40640 A1 | 12/1996 |
| WO | WO 98/27979 A1 | 7/1998 |
| WO | WO 99/64407 A1 | 12/1999 |
| WO | WO 00/32582 A1 | 6/2000 |
| WO | WO 01/05762 A2 | 1/2001 |
| WO | WO 01/97810 A2 | 12/2001 |
| WO | WO 02/20501 A2 | 3/2002 |

OTHER PUBLICATIONS

Wetterau J., Gregg r., Harrity t., Arbeeny c. Cap m. Connolly F., Chu C. Rocco G., David G. Jamil H. Jolibois K. ,Kunselman L, Lan S., Maccaganan T., Ricci B. Yan M., Young D., Chen Y. Fryszman O., Logan J., Musial C., Poss M., Robl J., Simpkins L., Slusarchyk W., Sulsky R, Taunk P., Magnin D., Tino J., Lawrence R., Dickson J., Biller S., An MTP Inhibitor That Normalize Atherogenic Lipoprotein Levels in WHHL Rabbits, Science, vol. 282 1998, pp. 751-754.
PCT Search Report dated Jun. 18, 2002 for PCT/EP 02/03491.
Sharp et al., "Cloning and gene defects in microsomal triglyceride transfer protein associated with abetalipoproteinemia.", Letters to Nature, 1993, vol. 365, pp. 65-69.
Hudson D., "Methodological Implications of Simultaneous Solid-Phase Peptide Synthesis. 1. Comparison of Different Coupling Procedures.", Journal of Organic Chemistry, 1988, vol. 53, pp. 617- 624.
Wiloughby et al., "Solid Phase Synthesis of Aryl Amines.", Tetrahedron Letters, 1996, vol. 37(40), pp. 7181-7184.
Wolfe et al., "An Improved Catalyst System for Aromatic Carbon-Nitrogen Bond Formation: The Possible Involvement of Bis(Phosphine) Palladium Complexes as Key Intermediates.", J. Am.Chem. Soc., 1996, vol. 118, pp. 7215-7216.
Chan et al., "New N- and O-Arylations with Phenylboronic Acids and Cupric Acetate.", Tetrahedron Letters, 1998, vol. 39, pp. 2933-1936.
Qureshi et al., "3-Hydroxy-3-methylglutaryl-CoA reductase from yeast.", Methods of Enzymology, 1981, vol. 71, pp. 455-509.
Miziorko, H.M., "3-Hydroxy-3-methylglutaryl-CoA synthase from chicken liver.", Methods of Enzymology, 1985, vol. 110, pp. 19-26.
Taylor et al., "Use of oxygenated sterols to probe the regulation of 3-hydroxy-3-methylglutaryl-CoA reductase and sterologenesis.", Methods of Enzymology, 1985, vol. 110, pp. 9-19.

(Continued)

Primary Examiner—Kamal A Saeed
Assistant Examiner—Shawquia Young

(57) ABSTRACT

Biphenylcarboxamide compounds of formula (I)

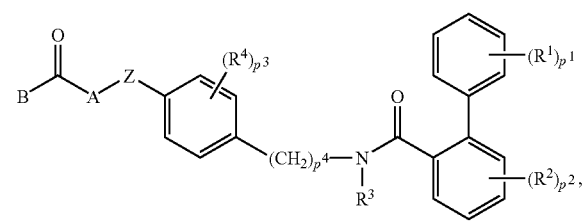

methods for preparing compounds of formula (I), pharmaceutical compositions comprising compounds of formula (I) as well as the use of compounds of formula (I) as a medicine for the treatment of hyperlipidemia, obesity and type II diabetes.

7 Claims, No Drawings

OTHER PUBLICATIONS

Agnew, W.S., "Squalene synthetase.", Methods of Enzymology, 1985, vol. 110, pp. 359-373.
Mercer, E.I., "Inhibitors of sterol biosynthesis and their applications.", Progress in Lipid Research, 1993, 32(4), pp. 357-416.
Kim et al., "Inhibition of Cholesteryl Ester Transfer Protein by Rosenonolactone Derivatives.", J.Antibioti., 1996, vol. 49(8), pp. 815-816.
Pietzonka et al., "Phosphonate-containing analogs of cholesteryl ester as novel inhibitors of cholesteryl ester transfer protein.", Bioorg. Med. Chem. Lett., 1996, vol. 6(16), pp. 1951-1954.
Heider et al., "Role of acyl CoA:cholesterol acyltransferase in cholesterol absorption and its inhibition by 57-1 18 in the rabbit.", Journal of Lipid Research, 1983, vol. 24, pp. 1127-1134.

* cited by examiner

LIPID LOWERING BIPHENYLCARBOXAMIDES

CROSS REFERENCE TO RELATED APPLICATIONS

This application is the national stage of Application No. PCT/EP02/03491, filed Mar. 27, 2002, which application claims priority from EP 01201270.4, filed Apr. 6, 2001.

The present invention is concerned with novel biphenylcarboxamide compounds having apolipoprotein B inhibiting activity and concomitant lipid lowering activity. The invention further relates to methods for preparing such compounds, pharmaceutical compositions comprising said compounds as well as the use of said compounds as a medicine for the treatment of hyperlipidemia, obesity and type II diabetes.

Obesity is the cause of a myriad of serious health problems like the adult onset of diabetes and heart disease. In addition, the loss of weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia. Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. The inconvenience of administration (a granular form to be dispersed in water or orange juice) and the major side-effects (gastro-intestinal discomfort and constipation) of bile acid sequestrant resins constitute major drawbacks. Fibric acid derivatives induce a moderate decrease (by 5 to 25%) of LDL cholesterol (except in hypertriglyceridemic patients in whom initially low levels tend to increase) and, although usually well tolerated, suffer from side-effects including potentiation of warfarine, pruritus, fatigue, headache, insomnia, painful reversible myopathy and stiffness in large muscle groups, impotency and impaired renal function. Nicotinic acid is a potent lipid lowering agent resulting in a 15 to 40% decrease in LDL cholesterol (and even 45 to 60% when combined with a bile acid sequestrant resin) but with a high incidence of troublesome side-effects related to the drug's associated vasodilatory action, such as headache, flushing, palpitations, tachychardia and occasional syncopes, as well as other side-effects such as gastro-intestinal discomfort, hyperucemia and impairment of glucose tolerance. Among the family of HMG Co-enzyme-A reductase inhibitors, lovastatin and simvastatin are both inactive prodrugs containing a lactone ring which is hydrolyzed in the liver to form the corresponding active hydroxy-acid derivative. Inducing a reduction of LDL cholesterol by 35 to 45%, they are generally well tolerated with a low incidence of minor side effects. However there still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of a coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, so named because it appears to be about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia.

Primary hyperlipidemias have also been classified into common hypercholesterolaemia, familial combined hyperlipidaemia, familial hypercholesterolaemia, remnant hyperlipidaemia, chylomicronaemia syndrome and familial hypertriglyceridaemia.

Microsomal triglyceride transfer protein (hereinafter referred as MTP) is known to catalyze the transport of triglyceride and cholesteryl ester by preference to phospholipids such as phosphatidylcholine. It was demonstrated by D. Sharp et al., *Nature* (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans. MTP inhibitors have been reported in Canadian patent application No. 2,091,102 and in WO 96/26205. MTP inhibitors belonging to the class of polyarylcarboxamides have also been reported in U.S. Pat. No. 5,760,246 as well as in WO-96/40640 and WO-98/27979.

One of the goals of the present invention is to provide an improved treatment for patients suffering from obesity or atherosclerosis, especially coronary atherosclerosis and more generally from disorders which are related to atherosclerosis, such as ischaemic heart disease, peripheral vascular disease and cerebral vascular disease. Another goal of the present invention is to cause regression of atherosclerosis and inhibit its clinical consequences, particularly morbidity and mortality.

The present invention is based on the unexpected discovery that a class of novel biphenylcarboxamide compounds is acting as selective MTP inhibitors, i.e. is able to selectively block MTP at the level of the gut wall in mammals, and is therefore a promising candidate as a medicine, namely for the treatment of hyperlipidemia. The present invention additionally provides several methods for preparing such biphenylcarboxamide compounds, as well as pharmaceutical compositions including such compounds. Furthermore, the invention provides a certain number of novel compounds which are useful intermediates for the preparation of the therapeutically active biphenylcarboxamide compounds, as well as methods for preparing such intermediates. Finally, the invention provides a method of treatment of a condition selected from atherosclerosis, pancreatitis, obesity, hypercholesterolemia, hypertriglyceridemia, hyperlipidemia, diabetes and type II diabetes, comprising administering a therapeutically active biphenylcarboxamide compound to a mammal.

The present invention relates to a family of novel compounds of formula (I)

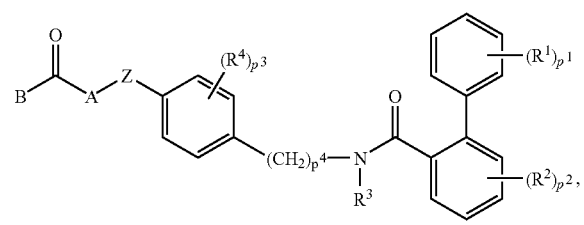

(I)

the N-oxides, the pharmaceutically acceptable acid addition salts and the stereochemically isomeric forms thereof, wherein $p^1$, $p^2$ and $p^3$ are integers each independently from 1 to 3;
$p^4$ is an integer zero or 1;
each $R^1$ is independently selected from hydrogen, $C_{1-4}$alkyl, $C_{1-4}$alkyloxy, halo, hydroxy, mercapto, cyano, nitro, $C_{1-4}$alkylthio or polyhalo$C_{1-6}$alkyl, amino, $C_{1-4}$alkylamino and di($C_{1-4}$alkyl)amino;
each $R^2$ is independently selected from hydrogen, $C_{1-4}$alkyl, $C_{1-4}$alkyloxy, halo, or trifluoromethyl;
$R^3$ is hydrogen or $C_{1-4}$alkyl;
each $R^4$ is independently selected from $C_{1-4}$alkyl, $C_{1-4}$alkyloxy, halo, or trifluoromethyl;
Z is a bivalent radical of formula

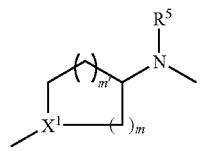

(a-1)

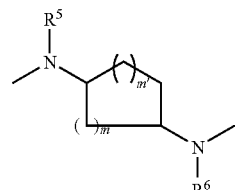

(a-2)

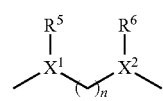

(a-3)

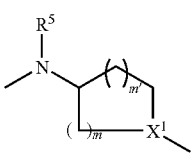

(a-4)

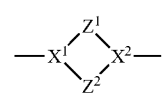

(a-5)

wherein n is an integer from 2 to 4;
m and m' are integers from 1 to 3;
$R^5$ and $R^6$ are each independently selected from hydrogen, $C_{1-6}$alkyl or aryl;
$X^1$ and $X^2$ are each independently selected from CH, N or an sp$^2$ hybridized carbon atom and in radical (a-1) at least one of $X^1$ or $X^2$ is N;
$Z^1$ is selected from $CH_2$, $CH_2CH_2$, $CH_2CH_2CH_2$, $CH_2CH_2O$ and $OCH_2CH_2$;
$Z^2$ is $CH_2$ or $CH_2CH_2$;
A represents a bond, $C_{1-6}$alkanediyl optionally substituted with one or two groups selected from aryl, heteroaryl and $C_{3-6}$cycloalkyl;
provided that when the bivalent radical Z is of formula (a-5) then A represents $C_{1-6}$alkanediyl substituted with one or two groups selected from aryl, heteroaryl and $C_{3-6}$cycloalkyl;
B represents a radical of formula

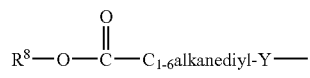

(b-1)

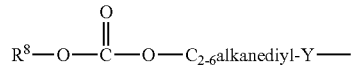

(b-2)

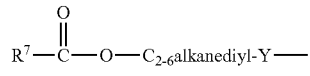

(b-3)

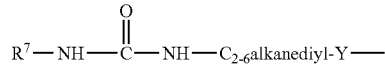

(b-4)

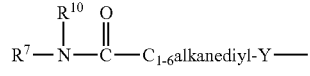

(b-5)

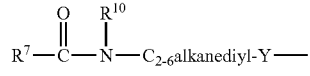

(b-6)

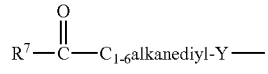

(b-7)

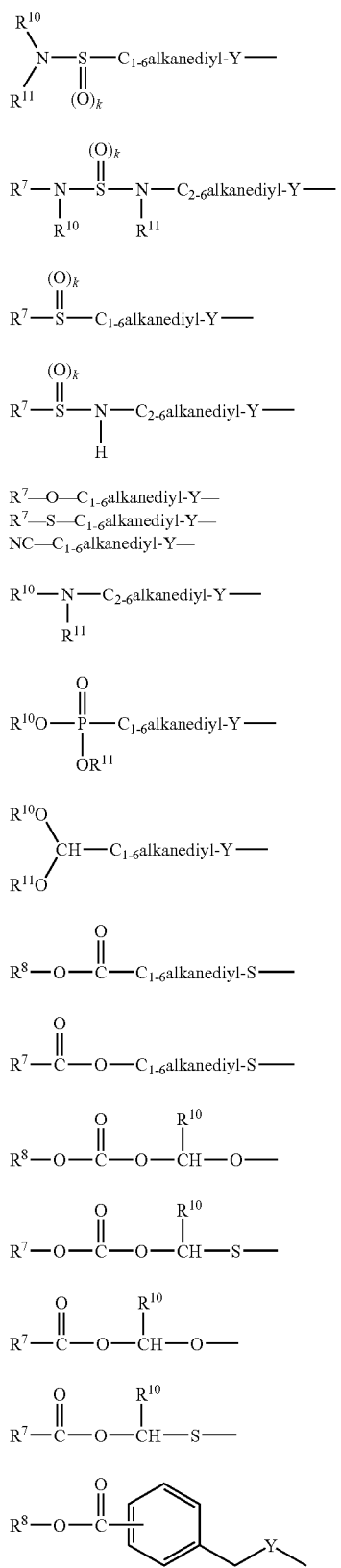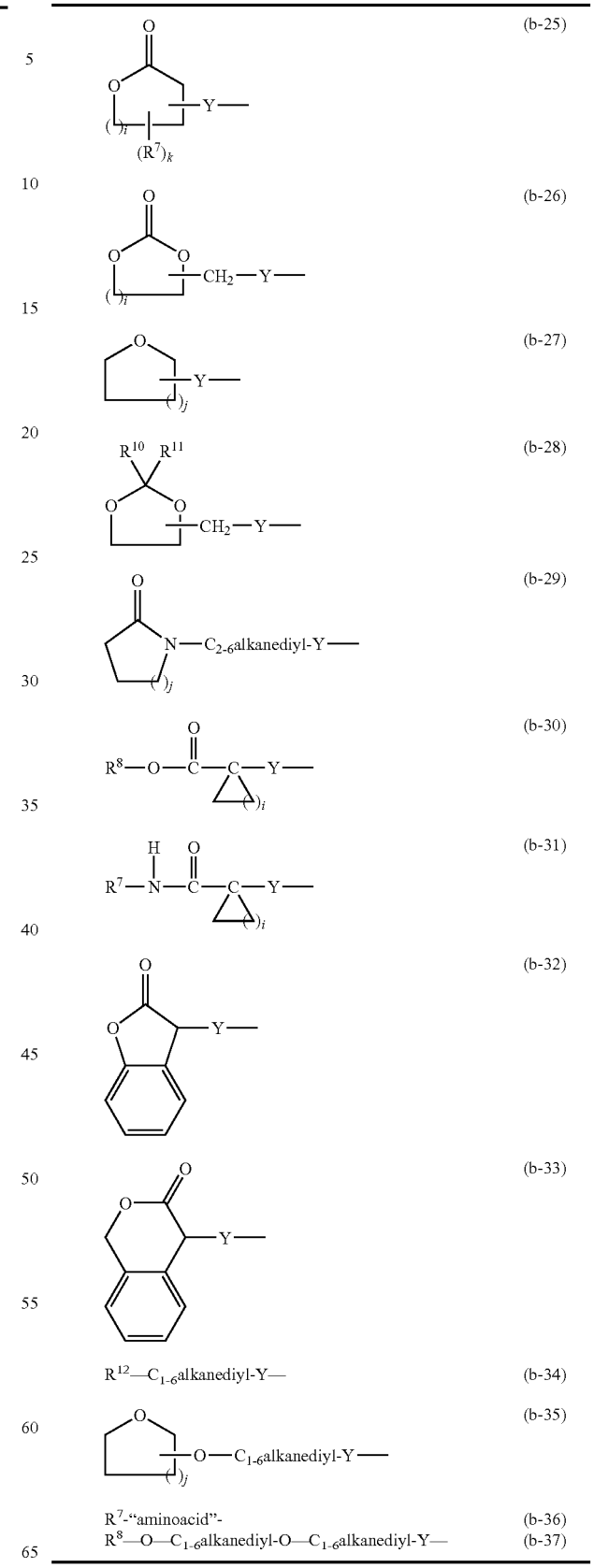

wherein i is an integer 1 to 4;
j is an integer 1 to 4;
k is an integer 1 or 2;
Y is O or $NR^9$ wherein $R^9$ is hydrogen, $C_{1-6}$alkyl or $C_{1-4}$alkylaminocarbonyl;
$R^7$ is hydrogen, $C_{1-6}$alkyl, $C_{2-6}$alkenyl, $C_{2-6}$alkynyl, phenyl, or phenyl substituted with $C_{1-4}$alkyl, halo, hydroxy or trifluoromethyl;
$R^8$ is $C_{1-6}$alkyl, $C_{2-6}$alkenyl, $C_{2-6}$alkynyl, phenyl, or phenyl substituted with $C_{1-4}$alkyl, halo, hydroxy or trifluoromethyl;
$R^{10}$ and $R^{11}$ are each independently hydrogen or $C_{1-6}$alkyl;
optionally $R^7$ and $R^9$ can be taken together to form a bivalent radical of formula —$(CH_2)_3$—, —$(CH_2)_4$—, —$(CH_2)_5$—, or —$(CH_2)_6$—;
$R^{12}$ is a radical of formula

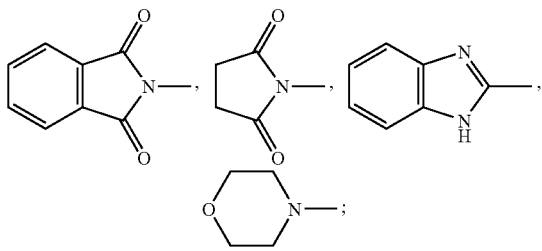

and optionally in radical (b-1) the $C_{1-6}$alkanediyl moiety can be further substituted with phenyl, phenyl$C_{1-4}$alkyl, hydroxyphenyl$C_{1-4}$alkyl, $C_{1-4}$alkyloxycarbonyl, $C_{1-4}$alkyloxy$C_{1-4}$alkyl, $C_{1-4}$alkylthio$C_{1-4}$alkyl, phenyl$C_{1-4}$alkylthio$C_{1-4}$alkyl, hydroxy$C_{1-4}$alkyl, thio$C_{1-4}$alkyl, $C_{3-6}$cycloalkyl, $C_{3-6}$cycloalkyl$C_{1-4}$alkyl, or a radical of formula

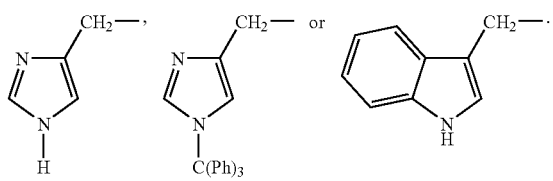

Unless otherwise stated, as used in the foregoing definitions and hereinafter:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, n-butyl, 1-methylethyl, 2-methylpropyl, 1,1-dimethylethyl and the like;
$C_{1-6}$alkyl is meant to include $C_{1-4}$alkyl (as hereinabove defined) and the higher homologues thereof having 5 or 6 carbon atoms, such as for instance 2-methylbutyl, n-pentyl, dimethylpropyl, n-hexyl, 2-methylpentyl, 3-methylpentyl and the like;
$C_{2-6}$alkenyl defines straight and branched chain unsaturated hydrocarbon radicals having from 2 to 6 carbon atoms, such as ethenyl, propenyl, butenyl, pentenyl or hexenyl;
$C_{2-6}$alkynyl defines straight and branched chain unsaturated hydrocarbon radicals having from 2 to 6 carbon atoms, such as ethynyl, propynyl, butynyl, pentynyl or hexynyl;
$C_{3-6}$cycloalkyl is generic to cyclopropyl, cyclobutyl, cyclopentyl, and cyclohexyl;

polyhalo$C_{1-6}$alkyl is defined as polyhalosubstituted $C_{1-6}$alkyl, in particular $C_{1-6}$alkyl (as hereinabove defined) substituted with 2 to 13 halogen atoms such as difluoromethyl, trifluoromethyl, trifluoroethyl, octafluoropentyl and the like;
aryl is defined as mono- and polyaromatic groups such as phenyl optionally substituted with one to three substituents each independently selected from nitro, azido, cyano, halo, hydroxy, $C_{1-6}$alkyl, $C_{3-6}$cycloalkyl, $C_{1-4}$alkyloxy, polyhalo$C_{1-6}$alkyl, amino, mono- or di($C_{1-6}$alkyl)amino;
heteroaryl is defined as mono- and polyheteroaromatic groups such as those including one or more heteroatoms selected from nitrogen, oxygen, sulfur and phosphorus, in particular pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl and the like, including all possible isomeric forms thereof, and optionally substituted with one or more substituents each independently selected from nitro, azido, cyano, halo, hydroxy, $C_{1-6}$alkyl, $C_{3-6}$cycloalkyl, $C_{1-4}$alkyloxy, polyhalo$C_{1-6}$alkyl, amino, mono- or di($C_{1-6}$alkyl)amino;
$C_{1-4}$alkylamino defines primary amino radicals having from 1 to 6 carbon atoms such as, for example, methylamino, ethylamino, propylamino, isopropylamino, butylamino, isobutylamino and the like;
di($C_{1-4}$alkyl)amino defines secondary amino radicals having from 1 to 6 carbon atoms such as, for example, dimethylamino, diethylamino, dipropylamino, diisopropylamino, N-methyl-N'-ethylamino, N-ethyl-N'-propylamino and the like;
$C_{1-4}$alkylthio defines a $C_{1-4}$alkyl group attached to a sulfur atom, such as methylthio, ethylthio, propylthio, isopropylthio, butylthio and the like;
as used herein, the term "amino acid" is used in its broadest sense to mean the naturally occurring amino acids of general formula R—CH(COOH)—$NH_2$ (i.e. glycine, alanine, valine, leucine, isoleucine, methionine, proline, phenylanaline, tryptophan, serine, threonine, cysteine, tyrosine, asparagine, glutamine, aspartic acid, esters of aspartic acid, glutamic acid, esters of glutamic acid, lysine, arginine, and histidine) as well as non-naturally occurring amino acids, including amino acid analogs. Thus, reference herein to an amino acid includes, for example, naturally occurring proteogenic (L)-amino acids, as well as (D)-amino acids, chemically modified amino acids such as amino acid analogs, naturally occurring non-proteogenic amino acids such as norleucine, lanthionine or the like, and chemically synthesized compounds having properties known in the art to be characteristic of an amino can be incorporated into a protein in a cell through a metabolic pathway. Said "amino acids" are linked via their carbonyloxy group to radical $R^7$ and via the nitrogen atom to the rest of the molecule (i.e. $R^7$—OOC—CRH—NH—).

Examples of the bivalent radical Z of formula (a-1) wherein one of $X^1$ or $X^2$ represents an $sp^2$ hybridized carbon atom are:

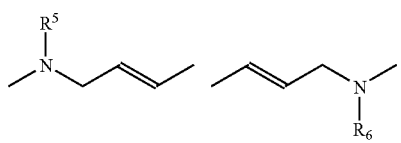

Examples of the bivalent radical Z of formula (a-5) are:

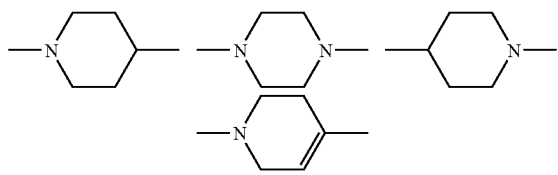

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein a nitrogen atom is oxidized to the N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

The terms cis and trans are used herein in accordance with Chemical Abstracts nomenclature and refer to the position of the substituents on a ring moiety.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

A group of interesting compounds consists of those compounds of formula (I) wherein one or more of the following restrictions apply:
a) $R^1$ is hydrogen, tert-butyl or trifluoromethyl;
b) $R^2$ is hydrogen;
c) $R^3$ is hydrogen;
d) $R^4$ is hydrogen;
e) $p^1$ is 1;
f) $p^2$ is 1;
g) $p^3$ is 1;
h) Z is a bivalent radical of formula (a-1) wherein $X^1$ and $X^2$ are each nitrogen;
i) Z is a bivalent radical of formula (a-2) wherein $X^1$ is nitrogen and m and m' are the integer 1;
j) Z is a bivalent radical of formula (a-2) wherein $X^1$ is nitrogen, m is the integer 2 and m' is the integer 1;
k) Z is a bivalent radical of formula (a-3) wherein $X^1$ is nitrogen and m and m' are the integer 1;
l) Z is a bivalent radical of formula (a-3) wherein $X^1$ is nitrogen, m is the integer 2 and m' is the integer 1;
m) Z is the bivalent radical of formula (a-4) wherein m is the integer 2 and m' is the integer 1;
n) Z is the bivalent radical of formula (a-5) wherein $Z^1$ and $Z^2$ represent $CH_2CH_2$;
o) $R^5$ and $R^6$ are each independently hydrogen or methyl;
p) the bivalent radical A is $C_{1-6}$alkanediyl substituted with one aryl group, in particular A is a methylene group substituted with phenyl;
q) B is a radical of formula (b-1).

A particular group of compounds are those compounds of formula (I) wherein the bivalent radical A represents a methylene group substituted with phenyl.

Another particular group of compounds are those compounds of formula (I) wherein Z is a bivalent radical of formula (a-5) wherein $Z^1$ and $Z^2$ represent $CH_2CH_2$ and $X^1$ is N and $X^2$ is CH.

Yet another particular group of compounds are those compounds of formula (I) wherein Z is a bivalent radical of formula (a-5) wherein $Z^1$ and $Z^2$ represent $CH_2CH_2$ and $X^1$ is CH and $X^2$ is N.

Still another particular group of compounds are those compounds of formula (I) wherein Z is a bivalent radical of formula (a-5) wherein $Z^1$ and $Z^2$ represent $CH_2CH_2$ and $X^1$ and $X^2$ are N.

A first process for preparing a biphenylcarboxamide compound according to this invention is a process wherein an intermediate phenylene amine having the formula

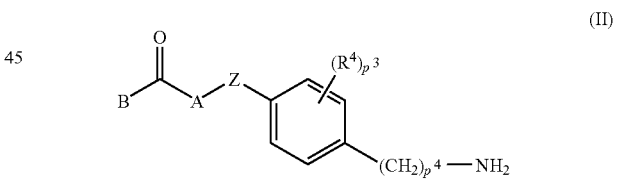

(II)

wherein B, A, Z and $R^4$ are as defined in formula (I), is reacted with a biphenylcarboxylic acid or halide having the formula (III),

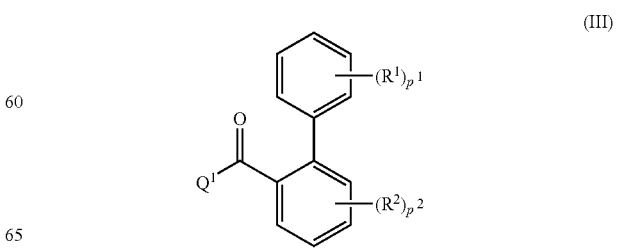

(III)

wherein $R^1$ and $R^2$ are as defined in formula (I) and $Q^1$ is selected from hydroxy and halo, in at least one reaction-inert solvent and optionally in the presence of a suitable base, the said process further optionally comprising converting a compound of formula (I) into an addition salt thereof, and/or preparing stereochemically isomeric forms thereof. In case $Q^1$ is hydroxy, it may be convenient to activate the biphenylcarboxylic acid of formula (III) by adding an effective amount of a reaction promoter. Non-limiting examples of such reaction promoters include carbonyldiimidazole, diimides such as N,N'-dicyclohexylcarbodiimide or 1-(3-dimethylaminopropyl)-3-ethylcarbodiimide, and functional derivatives thereof. For this type of acylation procedure, it is preferred to use a polar aprotic solvent such as, for instance, methylene chloride. Suitable bases for carrying out this first process include tertiary amines such as triethylamine, triisopropylamine and the like. Suitable temperatures for carrying out the first process of the invention typically range from about 20° C. to about 140° C., depending on the particular solvent used, and will most often be the boiling temperature of the said solvent.

A second process for preparing a biphenylcarboxamide compound of the invention is a process wherein an intermediate having the formula (IV)

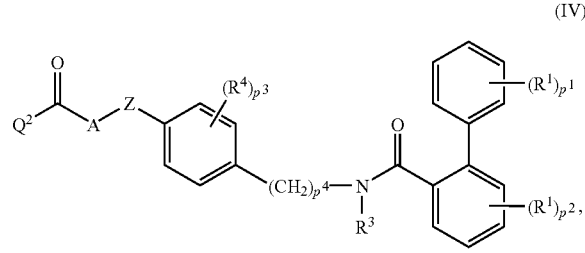

wherein $R^1$, $R^2$, $R^3$, $R^4$, A and Z are as defined in formula (I) and $Q^2$ is selected from halo and hydroxy, is reacted with an intermediate (V) of the formula B-H in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof. In case $Q^2$ is hydroxy, it may be convenient to activate the carboxylic acid of formula (IV) by adding an effective amount of a reaction promoter. Non-limiting examples of such reaction promoters include carbonyldiimidazole, diimides such as N,N'-dicyclohexylcarbodiimide or 1-(3-dimethylaminopropyl)-3-ethylcarbo-diimide, and functional derivatives thereof. In case a chirally pure reactant of formula (V) is used, a fast and enantiomerization-free reaction of the intermediate of formula (IV) with the said intermediate (V) may be performed in the further presence of an effective amount of a compound such as hydroxybenzotriazole, benzotriazolyloxytris(dimethylamino)phosphonium hexafluorophosphate, tetrapyrrolidinophosphonium hexafluorophosphate, bromotripyrrolidinophosphonium hexafluorophosphate, or a functional derivative thereof, such as disclosed by D. Hudson, *J. Org. Chem.* (1988), 53:617.

A third process for preparing a biphenylcarboxamide compound according to this invention is a process wherein an intermediate having the formula (VI)

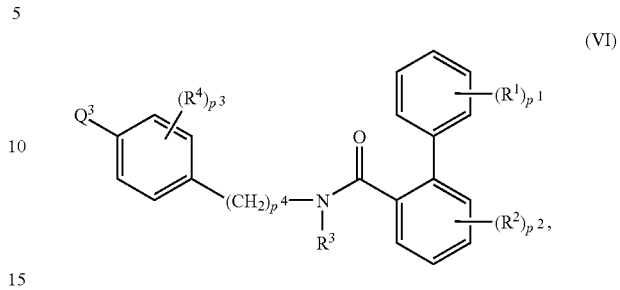

wherein $R^1$, $R^2$, $R^3$, and $R^4$ are as defined in formula (I) and $Q^3$ is selected from halo, $B(OH)_2$, alkylboronates and cyclic analogues thereof, is reacted with a reactant having the formula (VII)

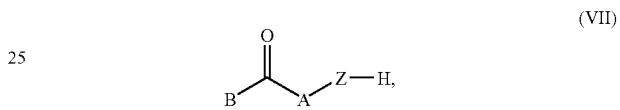

wherein B, A and Z are as defined in formula (I), in at least one reaction-inert solvent and optionally in the presence of at least one transition metal coupling reagent and/or at least one suitable ligand, the said process further optionally comprising converting a compound of formula (I) into an addition salt thereof, and/or preparing stereochemically isomeric forms thereof. This type of reaction being known in the art as the Buchwaldt reaction, reference to the applicable metal coupling reagents and/or suitable ligands, e.g. palladium compounds such as palladium tetra(triphenylphosphine), tris (dibenzylidene-acetone dipalladium, 2,2'-bis (diphenylphosphino)-1,1'-binaphthyl (BINAP) and the like, may be found for instance in *Tetrahedron Letters*, (1996), 37(40), 7181-7184 and *J. Am. Chem. Soc.*, (1996), 118:7216. If $Q^3$ is $B(OH)_2$, an alkylboronate or a cyclic analogue thereof, then cupric acetate should be used as the coupling reagent, according to *Tetrahedron Letters*, (1998), 39:2933-6.

The compounds of formula (I) can conveniently be prepared using solid phase synthesis techniques as depicted in Scheme 1 below. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry are described in for example "The Combinatorial Index" (B. Bunin, Academic Press) and Novabiochem's 1999 Catalogue & Peptide Synthesis Handbook (Novabiochem AG, Switzerland) both incorporated herein by reference.

Scheme 1:
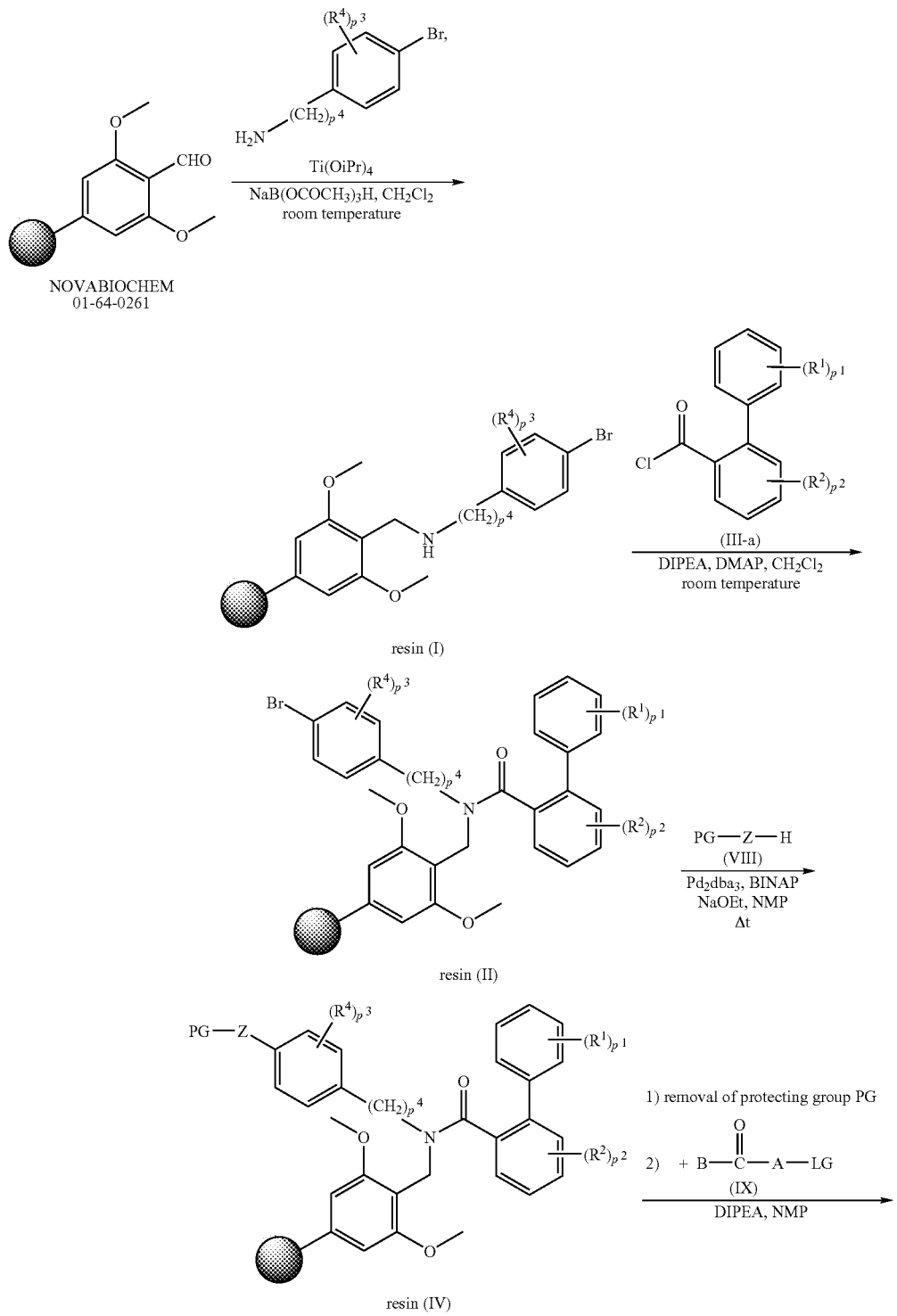

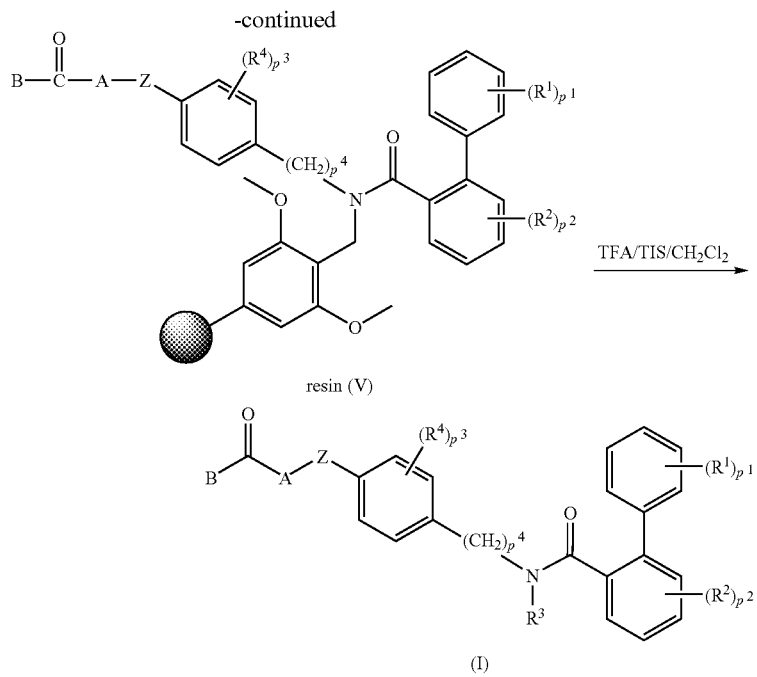

The abbreviations used in Scheme 1 are explained in the Experimental Part. The substituents $R^1$, $R^2$, $R^3$, $R^4$, A, B, and Z are as defined for compounds of formula (I). PG represents a protecting group such as, e.g. t-butoxycarbonyl, $C_{1-6}$alkyloxycarbonyl, phenylmethyloxycarbonyl, Fmoc and the like.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The biphenylcarboxamide compounds of formula (I), the N-oxide forms, the pharmaceutically acceptable salts and stereoisomeric forms thereof possess favourable apolipoprotein B inhibiting activity and concomitant lipid lowering activity. Therefore the present compounds are useful as a medicine especially in a method of treating patients suffering from hyperlipidemia, obesity, atherosclerosis or type II diabetes. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

The causal relationship between hypercholesterolemia—particularly that associated with increased plasma concentrations of low density lipoproteins (LDL) and very low density lipoproteins (VLDL)—and premature atherosclerosis and cardiovascular disease is well established. VLDL is secreted by the liver and contains apolipoprotein B (apo-B); these particles undergo degradation in the circulation to LDL, which transports about 60 to 70% of the total serum cholesterol. Apo-B is also the principal protein component of LDL. Increased LDL-cholesterol in serum, due to oversynthesis or decreased metabolism, is causally related to atherosclerosis. In contrast, high density lipoproteins (HDL) which contain apolipoprotein A1, have a protective effect and are inversely correlated with risk of coronary heart disease. The HDL/LDL ratio is thus a convenient method of assessing the atherogenic potential of an individual's plasma lipid profile.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthesized by the intestine, is necessary for the assembly of chylomicrons and therefore has an obligatory role in the intestinal absorption of dietary fats. The present invention provides biphenylcarboxamide compounds which are acting as selective MTP inhibitors at the level of the gut wall.

Additionally the present invention provides pharmaceutical compositions comprising at least one pharmaceutically acceptable carrier and a therapeutically effective amount of a biphenylcarboxamide compound having the formula (I).

In order to prepare the pharmaceutical compositions of this invention, an effective amount of the particular compound, in base or addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The biphenylcarboxamide compounds of this invention may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The biphenylcarboxamide compounds of this invention may also be formulated in rectal compositions such as suppositories or retention enemas, e.g. containing conventional suppository bases such as cocoa butter and/or other glycerides.

The biphenylcarboxamide compounds of this invention may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such inhibition may be determined readily by one skilled in the art according to standard assays, i.e. Methods of Enzymology (1981) 71:455-509. Exemplary compounds are described e.g. in U.S. Pat. No. 4,231,938 (including lovastatin), U.S. Pat. No. 4,444,784 (including simvastatin), U.S. Pat. No. 4,739,073 (including fluvastatin), U.S. Pat. No. 4,346,227 (including pravastatin), EP-A-491,226 (including rivastatin) and U.S. Pat. No. 4,647,576 (including atorvastatin).

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one skilled in the art according to standard assays, i.e. Methods of Enzymology (1985) 110:19-26. Exemplary compounds are described e.g. in U.S. Pat. No. 5,120,729 relating to beta-lactam derivatives, U.S. Pat. No. 5,064,856 relating to spiro-lactone derivatives and U.S. Pat. No. 4,847,271 relating to oxetane compounds.

Any HMG-CoA reductase gene expression inhibitor may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly or may be biotransformed into compounds having the above-mentioned attributes by one or more enzymes in the cholesterol biosynthetic cascade or may lead to accumulation of a metabolite having the above-mentioned activities. Such regulation may be determined readily by one skilled in the art according to standard assays, i.e. Methods of Enzymology (1985) 110:9-19. Exemplary compounds are described e.g. in U.S. Pat. No. 5,041,432 and E. I. Mercer, *Prog. Lip. Res.* (1993) 32:357-416.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL. Exemplary compounds are described e.g. in U.S. Pat. No. 5,512,548, in *J. Antibiot.* (1996) 49(8):815-816 and *Bioorg. Med. Chem. Lett.* (1996) 6:1951-1954.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase. Such inhibition may be determined readily by one skilled in the art according to standard assays, i.e. the method of Heider et al., *Journal of Lipid Research* (1983) 24:1127. Exemplary compounds are described e.g. in U.S. Pat. No. 5,510,379, in WO 96/26948 and WO 96/10559.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase. Such inhibition may be determined readily by one skilled in the art according to standard methods, i.e. Methods of Enzymology (1985) 110:359-373. Exemplary compounds are described e.g. in EP-0,567,026, in EP-0,645,378 and in EP-0,645,377.

Those of skill in the treatment of hyperlipidemia will easily determine the therapeutically effective amount of a biphenylcarboxamide compound of this invention from the test results presented hereinafter. In general it is contemplated that a therapeutically effective dose will be from about 0.001 mg/kg to about 5 mg/kg of body weight, more preferably from about 0.01 mg/kg to about 0.5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular biphenylcarboxamide compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the biphenylcarboxamide compounds of the instant invention. The effective daily amount ranges mentioned hereinabove are therefore only guidelines.

EXPERIMENTAL PART

In the procedures described hereinafter the following abbreviations were used: "ACN" stands for acetonitrile; "THF" stands for tetrahydrofuran; "DCM" stands for dichloromethane; "DIPE" stands for diisopropylether; "DMF" means N,N-dimethylformamide; "PyBOP" means a complex of (T-4)-hexafluorophosphate($1^-$) (1-hydroxy-1H-benzotriazolato-O)tri-1-pyrrolidinyl-phosphorus($1^+$); and "DIPEA" means diisopropylethylamine.

Of some compounds of formula (I) the absolute stereochemical configuration was not experimentally determined. In those cases the stereochemically isomeric form which was first isolated is designated as "A" and the second as "B", without further reference to the actual stereochemical configuration.

A. Synthesis of the Intermediates

Example A.1 a) A mixture of 4-[4-(phenylmethyl)-1-piperazinyl]-benzenamine (0.3 mol) and triethylamine (0.36 mol) in DCM (1500 ml) was stirred at room temperature for 15 minutes. 4'-(Trifluoromethyl)-[1,1'-biphenyl]-2-carbonyl chloride (0.36 mol) was added dropwise over 30 minutes. The mixture was stirred at room temperature for 3 hours and then washed twice with water, then washed with a saturated NaCl solution. The organic layer was separated, dried, filtered and the solvent was evaporated. The residue was stirred in DIPE (800 ml). The precipitate was filtered off, washed twice with DIPE and dried in vacuo at 50° C., yielding 140.2 g of N-[4-[4-(phenylmethyl)-1-piperazinyl]phenyl]-4'-(trifluoromethyl)-[1,1'-biphenyl]-2-carboxamide (intermediate 1, mp. 180° C.).

b) A mixture of intermediate (1) (0.19 mol) in methanol (600 ml) and THF (600 ml) was hydrogenated overnight with palladium on carbon (10%; 3 g) as a catalyst. After uptake of hydrogen (1 equivalent), the catalyst was filtered off and the filtrate was evaporated. The residue was triturated in DIPE. The precipitate was filtered off and dissolved in water. The mixture was alkalized with Na$_2$CO$_3$ and then extracted with DCM. The organic layer was separated, dried, filtered and the solvent was evaporated. The residue was triturated in DIPE. The precipitate was filtered off and dried, yielding N-[4-(1-piperazinyl)phenyl]-4'-(trifluoromethyl)-[1,1'-biphenyl]-2-carboxamide (intermediate 2).

c) A mixture of intermediate (2) (0.007 mol) and Na$_2$CO$_3$ (0.007 mol) in DMF (50 ml) was stirred. Methyl 2-bromo-2-phenylacetate (0.007 mol) was added dropwise. The mixture was stirred for 4 hours. The solvent was evaporated. The residue was dissolved in DCM. The organic layer was separated, washed, dried, filtered and the solvent was evaporated. The residue was triturated in 2-propanol. The precipitate was filtered off and dried, yielding 3.34 g of methyl α-phenyl-4-[4-[[[4'-(trifluoromethyl)[1,1'-biphenyl]-2-yl]carbonyl]amino]phenyl]-1-piperazineacetate (intermediate 3).

d) A mixture of intermediate (3) (0.19 mol) in HCl (36%; 100 ml) was stirred and refluxed for 5 hours, then stirred overnight at room temperature. The precipitate was filtered off and triturated under 2-propanol, filtered off and dried, yielding 5 g of α-phenyl-4-[4-[[[4'-(trifluoromethyl)[1,1'-biphenyl]-2-yl]carbonyl]amino]phenyl]-1-piperazineacetic acid monohydrochloride (intermediate 4).

Example A.2 a) Methyl 2-bromo-2-phenylacetate (0.1 mol) was added dropwise to a mixture of 4-(1-piperazinyl)benzonitrile (0.1 mol) and Na$_2$CO$_3$ (90.15 mol) in DMF (250 ml), stirred at room temperature. The reaction mixture was stirred overnight. The solvent was evaporated. The residue was dissolved in DCM, washed, dried, filtered and the solvent evaporated. The residue was triturated under DIPE, filtered off and dried, yielding 26.5 g of 1-piperazineacetic acid, 4-(4-cyanophenyl)-α-phenyl-, methyl ester (intermediate 5).

b) A mixture of intermediate (5) (0.079 mol) in a mixture of methanol saturated with NH$_3$ (600 ml) was hydrogenated at 14° C. overnight with Raney nickel (1 g) as a catalyst. After uptake of hydrogen (2 equivalents), the catalyst was filtered off and the filtrate was evaporated. The residue was dissolved in 2-propanol. The mixture was acidified with a mixture HCl/2-propanol and then stirred overnight. The precipitate was filtered off and dried, yielding 26.7 g of 1-piperazineacetic acid, 4-[4-(aminomethyl)phenyl]-α-phenyl-, methyl ester hydrochloride (1:3) 2-propanolate (1:1) (intermediate 6).

c) A mixture of intermediate (6) (0.024 mol) in THF (250 ml) and triethylamine (50 ml) was stirred. 4'-(Trifluoromethyl)-[1,1'-biphenyl]-2-carbonyl chloride (0.026 mol) was added dropwise. The mixture was stirred overnight. The solvent was evaporated. The residue was purified by column chromatography over silica gel (eluent: CH$_2$Cl$_2$/CH$_3$OH 99/1). The pure fractions were collected and the solvent was evaporated. The residue was triturated in DIPE. The precipitate was filtered off and dried, yielding 7.7 g of 1-piperazineacetic acid, α-phenyl-4-[4-[[[4'-(trifluoromethyl)[1,1'-biphenyl]-2-yl]carbonyl]amino]methyl]phenyl]-, methyl ester (intermediate 7).

d) A mixture of intermediate (7) (0.012 mol) in HCl (36%; 100 ml) was stirred and refluxed overnight, then cooled, decanted and the residue was dissolved in methanol. The solvent was evaporated. The residue was triturated under DIPE, filtered off and dried, yielding 6.2 g of 1-piperazineacetic acid, α-phenyl-4-[4-[[[4'-(trifluoromethyl)[1,1'-biphenyl]-2-yl]carbonyl]amino]methyl]phenyl]-hydrochloride (1:1) (intermediate 8).

Example A.3 a) A mixture of 4'-(trifluoromethyl)-[1,1'-biphenyl]-2-carboxylic acid (0.09 mol) in DCM (500 ml) and DMF (5 ml) was stirred. Ethanedioyl dichloride (0.09 mol) was added dropwise. The mixture was stirred for 1 hour to give mixture (A). A mixture of 4-[1-(phenylmethyl)-4-piperidinyl]-benzenamine (0.046 mol) in DCM (500 ml) and triethylamine (20 ml) was stirred on an ice-bath. Mixture (A) was added dropwise. The mixture was stirred and refluxed overnight, then cooled and washed with water. The organic layer was separated, dried, filtered and the solvent was evaporated. The residue was purified by column chromatography over silica gel (eluent: CH$_2$Cl$_2$/CH$_3$OH 98/2). The pure fractions were collected and the solvent was evaporated. The residue was triturated in DIPE. The precipitate was filtered off and dried, yielding 5.6 g of N-[4-[1-(phenylmethyl)-4-piperidinyl]phenyl]-4'-(trifluoromethyl)-[1,1'-biphenyl]-2-carboxamide (intermediate 9, mp. 134° C.).

b) A mixture of intermediate (9) (0.025 mol) in methanol (250 ml) was hydrogenated at 50° C. overnight with palladium on carbon (10%; 2 g) as a catalyst. After uptake of hydrogen (1 equivalent), the catalyst was filtered off and the filtrate was evaporated. The residue was triturated in DIPE. The precipitate was filtered off and dried, yielding 7.7 g of N-[4-(4-piperidinyl)phenyl]-4'-(trifluoromethyl)-[1,1'-biphenyl]-2-carboxamide (intermediate 10).

c) A mixture of intermediate (10) (0.007 mol) and Na$_2$CO$_3$ (0.007 mol) in DMF (50 ml) was stirred at room temperature. Methyl 2-bromo-2-phenylacetate (0.007 mol) was added dropwise. The mixture was stirred for 3 hours. The solvent was evaporated. The residue was triturated under hexane, filtered off and dried, yielding 3.37 g of methyl α-phenyl-4-[4-[[[4'-(trifluoromethyl)[1,1'-biphenyl]-2-yl]carbonyl]amino]-phenyl]-1-piperidineacetate (intermediate 11, mp. 138° C.).

d) A mixture of intermediate (11) (0.012 mol) in HCl (36%, 100 ml) was stirred and refluxed for 6 hours, then stirred overnight at room temperature. The precipitate was filtered off and triturated under 2-propanol. The precipitate was filtered off and dried, yielding 6.2 g of α-phenyl-4-[4-[[[4'-(trifluoromethyl)[1,1'-biphenyl]-2-yl]carbonyl]-amino]phenyl]-1-piperidineacetic acid monohydrochloride (intermediate 12).

Example A.4 a) A mixture of 4-[4-(phenylmethyl)-1-piperazinyl]-benzenamine (0.12 mol) in THF (300 ml) and triethylamine (50 ml) was stirred. [1,1'-Biphenyl]-2-carbonyl chloride (0.12 mol) was added dropwise. The mixture was stirred overnight. The solvent was evaporated. The residue was dissolved in DCM. The organic layer was separated, washed, dried, filtered and the solvent was evaporated. The residue was triturated in DIPE/2-propanol. The precipitate was filtered off and dried, yielding 46.5 g of N-[4-[4-(phenylmethyl)-1-piperazinyl]phenyl]-[1,1'-bipehnyl]-2-carboxamide (intermediate 13, mp. 162° C.).

b) A mixture of intermediate (13) (0.1 mol) in methanol (500 ml) was hydrogenated for 2 hours with palladium on carbon (10%; 10 g) as a catalyst. After uptake of hydrogen (1 equivalent), the catalyst was filtered off and the filtrate was evaporated. The residue was triturated in 2-propanol. The precipitate was filtered off and dried, yielding 29 g of N-[4-(1-piperazinyl)phenyl]-[1,1'-biphenyl]-2-carboxamide (intermediate 14, mp. 176° C.).

Example A.5 a) A mixture of α-phenyl-4-piperidineacetonitrile monohydrochloride (0.05 mol), 1-fluoro-4-nitrobenzene (0.06 mol) and K$_2$CO$_3$ (0.15 mol) in DMF (200 ml) was stirred at 50° C. for 4 hours, cooled, poured out into water and extracted with DCM. The organic layer was separated, washed, dried, filtered and the solvent was evaporated. The residue was crystallized from DIPE. The precipitate was filtered off and dried, yielding 10.7 g of (±)-1-(4-nitrophenyl)-α-phenyl-4-piperidineacetonitrile (intermediate 15, mp. 118° C.).

b) A mixture of intermediate (15) (0.036 mol) in HBr (48%; 100 ml) was stirred and refluxed for 3 hours, cooled, poured out into water and extracted twice with DCM. The organic layer was separated, washed with water, dried, filtered and the solvent was evaporated. The residue was triturated with 2-propanol. The precipitate was filtered off and dried, yielding 9.5 g of (±)-1-(4-nitrophenyl)-α-phenyl-4-piperidineacetic acid (intermediate 16, mp. 216° C.).

c) Thionyl chloride (0.01 mol) was added to a mixture of intermediate (16) (0.0029 mol) in DCM (10 ml). The mixture was stirred overnight and then the solvent was evaporated. The residue was dissolved in DCM (10 ml). Methanol (10 ml) was added. The mixture was allowed to stand for 4 hours, then poured out into a NaHCO$_3$ solution and extracted with DCM. The organic layer was separated, dried, filtered and the solvent was evaporated. The residue was triturated in hexane/DIPE. The precipitate was filtered off and dried, yielding 0.9 g of (±)-methyl 1-(4-nitrophenyl)-α-phenyl-4-piperidineacetate (intermediate 17, mp. 124° C.).

d) A mixture of intermediate (17) (0.0022 mol) in methanol (100 ml) was hydrogenated at 50° C. with palladium on carbon (10%; 0.1 g) as a catalyst in the presence of a thiophene solution (4%; 0.1 ml). After uptake of hydrogen (3 equivalents), the catalyst was filtered off and the filtrate was evaporated. The residue was triturated in hexane. The precipitate was filtered off and dried, yielding 0.7 g (±)-methyl 1-(4-aminophenyl)-α-phenyl-4-piperidineacetate (intermediate 18, mp. 125° C.).

e) A mixture of 2-(4-tert-butylphenyl)benzoic acid (0.02 mol) and thionyl chloride (0.04 mol) and DMF (5 drops) in DCM (50 ml) was stirred and refluxed for 1 hour. The solvent was evaporated and DCM (2×50 ml) was added and again the solvent was evaporated. The residue was dissolved in DCM (50 ml) and added to a solution of intermediate (18) (0.02 mol) and DIPEA (0.04 mol) in DCM (50 ml). The reaction mixture was stirred at room temperature for 4 hours. The residue was purified by column chromatography over silica gel (eluent: CH$_2$Cl$_2$/CH$_3$OH 99.5/0.5). The product fractions were collected and the solvent was evaporated. The residue was dissolved in 2-propanol and DIPE and converted into the hydrochloric acid salt (1:1) with HCl/2-propanol. The residue was filtered off and dried, yielding 8.7 g of 4-piperidineacetic acid, 1-[4-[[[4'-(1,1-dimethylethyl)[1,1'-biphenyl]-2-yl]carbonyl]amino]phenyl]-α-phenyl-, methyl ester hydrochloride (1:1) 2-propanolate (1:1) (intermediate 19).

f) Intermediate (19) (0.0097 mol) in a concentrated HCl solution (30 ml) and dioxane (40 ml) was stirred and refluxed for 5 hours, then cooled. The precipitate was filtered off, washed with water and a small amount of 2-propanol and dried, yielding 5 g of 4-piperidineacetic acid, 1-[4-[[[4'-(1,1-dimethylethyl)[1,1'-biphenyl]-2-yl]carbonyl]amino]phenyl]-α-phenyl-hydrochloride (1:1) (intermediate 20).

Example A.6 a) DMF (0.5 ml) was added to a solution of 2-biphenylcarboxylic acid (0.077 mol) in DCM (250 ml). Thionyl chloride (0.154 mol) was added. The mixture was stirred and refluxed for 1 hour. The solvent was evaporated and then co-evaporated twice with DCM (100 ml). The residue was dissolved in DCM (100 ml) to give solution (A). Intermediate (18) (0.077 mol) and DIPEA (0.154 mol) were stirred in DCM (400 ml). Solution (A) was added. The mixture was stirred at room temperature for 3 hours and then washed with water. The organic layer was separated, dried, filtered and the solvent was evaporated, yielding 44 g of 4-piperidineacetic acid, 1-[4-[([1,1'-biphenyl]-2-ylcarbonyl)amino]phenyl]-α-phenyl-, methyl ester (intermediate 21).

b) A mixture of intermediate (21) (0.013 mol) in HCl (36%; 200 ml) and dioxane (150 ml) was stirred and refluxed overnight. The reaction mixture was cooled and water (300 ml) was added. The mixture was stirred for 1 hour and filtered. The residue was dissolved in DCM and MeOH and the solvent was evaporated. The residue was triturated in DIPE and 2-propanol, yielding 3.5 g of 4-piperidineacetic acid, 1-[4-

[([1,1'-biphenyl]-2-ylcarbonyl)amino]phenyl]-α-phenyl-hydrochloride (1:1) (intermediate 22).

Example A.7 a) Thionyl chloride (3.6 ml) was added to a clear solution of 4'-(trifluoromethyl)-[1,1'-biphenyl]-2-carboxylic acid (0.025 mol) in DMF (1 ml) and DCM (100 ml). The mixture was stirred and refluxed for one hour. The solvent was evaporated. DCM (50 ml) was added to the residue, then evaporated. The residue was dissolved in DCM (50 ml) and the solution was added dropwise to a solution of intermediate (18) (0.025 mol) in DCM (150 ml) and DIPEA (0.049 mol). The reaction mixture was stirred for 2 hours at room temperature. Water was added and this mixture was extracted twice. The separated organic layer was dried, filtered and the solvent evaporated. The residue was stirred in DIPE, filtered off, dried, and crystallized from 2-propanol (150 ml; later, 300 ml was added). The mixture was stirred for 2 hours at room temperature. The precipitate was filtered off, washed with 2-propanol and dried, yielding 8.58 g of methyl α-phenyl-1-[4-[[[4'-(trifluoromethyl)[1,1'-biphenyl]-2-yl]carbonyl]amino]phenyl]-4-piperidineacetate (intermediate 23).

b) A mixture of intermediate (23) (0.0014 mol) in concentrated HCl (25 ml) and dioxane (20 ml) was stirred and refluxed for 4 hours, cooled and poured out into water. The mixture was extracted with DCM. The organic layer was separated, dried, filtered and the solvent was evaporated. The residue was triturated in DIPE. The precipitate was filtered off and dried, yielding 0.48 g of α-phenyl-1-[4-[[[4'-(trifluoromethyl)[1,1'-biphenyl]-2-yl]carbonyl]amino]phenyl]-4-piperidineacetic acid monohydrochloride (intermediate 24, mp. 196° C.).

Example A.8 a) Intermediate (23) was separated (and purified) in its enantiomers by chiral column chromatography over Chiralcel OD (1000 Å, 20 μm, Daicel; eluent: (80/13/7) hexane/ethanol/methanol).

The first fraction was further purified by high-performance liquid chromatography over RP BDS (Hyperprep C18 (100 Å, 8 μm; eluent: [(0.5% NH$_4$OAc in H$_2$O)/CH$_3$CN 90/10)]/CH$_3$OH/CH$_3$CN (0 min) 30/70/0, (24 min) 0/100/0, (24.01 min) 0/0/100, (32 min) 30/70/0) and crystallisation from 2-propanol, yielding (A)-α-phenyl-1-[4-[[[4'-(trifluoromethyl)[1,1'-biphenyl]-2-yl]carbonyl]amino]phenyl]-4-piperidineacetate (intermediate 25).

The second fraction was further purified by high-performance liquid chromatography over RP BDS (Hyperprep C18 (100 Å, 8 μm; eluent: [(0.5% NH$_4$OAc in H$_2$O)/CH$_3$CN 90/10)]/CH$_3$OH/CH$_3$CN (0 min) 30/70/0, (24 min) 0/100/0, (24.01 min) 0/0/100, (32 min) 30/70/0) and crystallisation from 2-propanol, yielding (B)-α-phenyl-1-[4-[[[4'-(trifluoromethyl)[1,1'-biphenyl]-2-yl]carbonyl]amino]phenyl]-4-piperidineacetate (intermediate 26).

b) Using the procedure of Example A.7 b) intermediate (25) was converted into (A)-α-phenyl-1-[4-[[[4'-(trifluoromethyl)[1,1'-biphenyl]-2-yl]carbonyl]amino]-phenyl]-4-piperidineacetic acid monohydrochloride (intermediate 27, mp. 140° C., $[\alpha]_D^{20}$=+17.06° (c=9.67 mg/5 ml in CH$_3$OH)).

c) Using the procedure of Example A.7 b) intermediate (26) was converted into (B)-α-phenyl-1-[4-[[[4'-(trifluoromethyl)[1,1'-biphenyl]-2-yl]carbonyl]amino]-phenyl]-4-piperidineacetic acid monohydrochloride (intermediate 28, mp. 135° C., $[\alpha]_D^{20}$=−27.10° (c=11.07 mg/5 ml in CH$_3$OH)).

Example A.9 a) A mixture of intermediate (10) (0.019 mol) and Na$_2$CO$_3$ (0.019 mol) in DMF (125 ml) was stirred at room temperature. Methyl 2-bromo-2-phenylacetate (0.01907 mol) was added dropwise. The mixture was stirred for 3 hours. The solvent was evaporated. The residue was taken up in water and DCM. The separated organic layer was dried, filtered and the solvent was evaporated. The residue was purified by column chromatography over silica gel (eluent: CH$_2$Cl$_2$/CH$_3$OH 100/0; 99.5/0.5) and separated by high performance liquid chromatography over Chiralpak AD (eluent: hexane/ethanol 70/30) in its enantiomers. The desired fractions were collected and the solvent was evaporated, yielding 1-piperidineacetic acid, α-phenyl-4-[4-[[[4'-(trifluoromethyl)[1,1'-biphenyl]-2-yl]carbonyl]amino]phenyl]-, methyl ester, (α$^1$A)-(intermediate 29, mp. 158° C., $[\alpha]_D^{20}$=−28.86° (c=124.95 mg/5 ml in CH$_3$OH)) after crystallisation from 2-propanol and 1-piperidineacetic acid, α-phenyl-4-[4-[[[4'-(trifluoromethyl)[1,1'-biphenyl]-2-yl]carbonyl]amino]phenyl]-, methyl ester, (α$^1$B)-(intermediate 30, mp. 160° C., $[\alpha]_D^{20}$=+27.69° (c=24.38 mg/5 ml in CH$_3$OH)) after crystallisation from 2-propanol.

b) Using the procedure of Example A.7 b) intermediate (29) was converted into 1-piperidineacetic acid, α-phenyl-4-[4-[[[4'-(trifluoromethyl)[1,1'-biphenyl]-2-yl]carbonyl]amino]phenyl]-, (α$^1$A)-(intermediate 31, mp. 180° C., $[\alpha]_D^{20}$=−35.90° (c=25.21 mg/5 ml in CH$_3$OH)).

c) Using the procedure of Example A.7 b) intermediate (30) was converted into 1-piperidineacetic acid, α-phenyl-4-[4-[[[4'-(trifluoromethyl)[1,1'-biphenyl]-2-yl]carbonyl]amino]phenyl]-, (α$^1$B)-(intermediate 32, mp. 135° C., $[\alpha]_D^{20}$=+35.30° (c=23.94 mg/5 ml in CH$_3$OH)).

Example A.10 a) A mixture of intermediate (2) (0.019 mol) and Na$_2$CO$_3$ (0.019 mol) in DMF (125 ml) was stirred. Methyl 2-bromo-2-phenylacetate (0.019 mol) was added dropwise. The mixture was stirred at room temperature for 3 hours. The solvent was evaporated. The residue was stirred in DCM and washed with water. The separated organic layer was dried, filtered and the solvent was evaporated. The residue was stirred in DIPE. The precipitate was filtered off, dried and separated by high performance liquid chromatography over Chiralcel OD (eluent:hexane/EtOH 70/30) in its enantiomers. The desired fractions were collected and the solvent was evaporated, yielding 1-piperazineacetic acid, α-phenyl-4-[4-[[[4'-(trifluoromethyl)[1,1'-biphenyl]-2-yl]carbonyl]amino]phenyl]-, methyl ester, (α$^1$A)-(intermediate 33) after crystallisation from 2-propanol, and 1-piperazineacetic acid, α-phenyl-4-[4-[[[4'-(trifluoromethyl)[1,1'-biphenyl]-2-yl]carbonyl]amino]phenyl]-, methyl ester, (α$^1$B)-(intermediate 34) after crystallisation from 2-propanol.

b) Using the procedure of Example A.7 b) intermediate (33) was converted into 1-piperazineacetic acid, α-phenyl-4-[4-[[[4'-(trifluoromethyl)[1,1'-biphenyl]-2-yl]carbonyl]amino]phenyl]-, (α$^1$A)-(intermediate 35, mp. 230° C., $[\alpha]_D^{20}$=+60.15° (c=24.52 mg/5 ml in CH$_3$OH)).

c) Using the procedure of Example A.7 b) intermediate (34) was converted into 1-piperazineacetic acid, α-phenyl-4-[4-[[[4'-(trifluoromethyl)[1,1'-biphenyl]-2-yl]carbonyl]amino]phenyl]-, (α$^1$B)-(intermediate 36, mp. 232° C., $[\alpha]_D^{20}$=−66.37° (c=26.52 mg/5 ml in CH$_3$OH)).

Example A.11 a) Methyl 2-bromo-2-phenylacetate (0.1 mol) was added dropwise to a stirring mixture of intermediate (14) (0.07 mol) and Na$_2$CO$_3$ (13 g) in DMF (300 ml). The mixture was stirred overnight. The solvent was evaporated. The residue was crystallized from methanol. The precipitate was filtered off and dried, yielding 30.2 g of methyl 4-[4-[((1,1'-biphenyl]-2-ylcarbonyl)amino]phenyl]-α-phenyl-1-piperazineacetate (intermediate 37, mp. 125° C.).

b) A mixture of intermediate (37) (0.053 mol) in HCl (36%; 300 ml) was stirred and refluxed for 2 days, cooled, filtered and dried. The residue was triturated in 2-propanone. The precipitate was filtered off and dried, yielding 21.5 g of α-phenyl-4-[4-[([1,1'-biphenyl]-2-ylcarbonyl)amino]phenyl]-1-piperazineacetic acid hydrochloride (1:2) 2-propanolate (1:1) (intermediate 38).

Example A.12 a) 2-Biphenylcarboxylic acid (0.25 mol) was dissolved in DCM (500 ml) and DMF (0.5 ml). Thionyl chloride (0.51 mol) was added dropwise. The mixture was stirred and refluxed for 1 hour under nitrogen flow. The solvent was evaporated. DCM (500 ml) was added twice. The solvent was evaporated twice. The residue was dissolved in DCM (200 ml) and then added dropwise at 0° C. to a mixture of 4-[1-(phenylmethyl)-4-piperidinyl]-benzenamine (0.25 mol) and N-(1-methylethyl)-2-propanamine (0.75 mol) in DCM (800 ml). The mixture was brought to room temperature and then stirred at room temperature overnight under nitrogen flow. The mixture was washed three times with water (800 ml). The organic layer was separated, dried, filtered and the solvent was evaporated, yielding 125 g of [1,1'-biphenyl]-2-carboxamide, N-[4-[1-(phenylmethyl)-4-piperidinyl]phenyl]-(intermediate 39).

b) A mixture of intermediate (39) (0.145 mol) in methanol (500 ml) was hydrogenated at 50° C. over the weekend with palladium on carbon (10%; 3 g) as a catalyst. After uptake of hydrogen (1 equivalent), the catalyst was filtered off and the filtrate was evaporated. The residue was triturated in DIPE. The precipitate was filtered off and dried, yielding 49 g of [1,1'-biphenyl]-2-carboxamide, N-[4-(4-piperidinyl)phenyl]-(intermediate 40).

c) A mixture of intermediate (40) (0.0084 mol) and Na$_2$CO$_3$ (0.01 mol) in DMF (150 ml) was stirred. Methyl 2-bromo-2-phenylacetate (0.01 mol) was added dropwise. The mixture was stirred overnight. The solvent was evaporated. The residue was dissolved in DCM. The organic layer was separated, washed, dried, filtered and the solvent was evaporated. The residue was purified by column chromatography over silica gel (eluent: DCM 100%). The pure fractions were collected and the solvent was evaporated. The residue was triturated in DIPE. The precipitate was filtered off and dried, yielding 2.79 g of 1-piperidineacetic acid, 4-[4-[([1,1'-biphenyl]-2-ylcarbonyl)amino]phenyl]-α-phenyl-, methyl ester (intermediate 41).

d) Intermediate (41) (0.003 mol) in HCl (36%; 25 ml) and dioxane (10 ml) was stirred and refluxed overnight. The solvent was evaporated. The residue was triturated in DIPE and 2-propanol; then recrystallized from ACN. The precipitate was filtered off, dried and purified by high performance liquid chromatography over RP BDS C18 (eluent: (0.5% NH$_4$OAc in H$_2$O/CH$_3$CN 90/10)/MeOH/CH$_3$CN 75/25/0; 0/50/50; 0/0/100). The pure fractions were collected and the solvent was evaporated. The residue was triturated in DIPE, yielding 0.5 g of 1-piperidineacetic acid, 4-[4-[([1,1'-biphenyl]-2-ylcarbonyl)amino]phenyl]-α-phenyl-(intermediate 42). Acetic acid, [[phenyl[1-[4-[[[4'-(trifluoromethyl)[1,1'-biphenyl]-2-yl]carbonyl]-amino]phenyl]-4-piperidinyl]acetyl]amino]-(intm. 45) was prepared analogously by hydrolyzing compound (18) according to the method as described above.

Acetic acid, [[phenyl[4-[4-[[[4'-(trifluoromethyl)[1,1'-biphenyl]-2-yl]carbonyl]-amino]phenyl]-1-piperazinyl] acetyl]amino]-(intm. 46) was prepared analogously by hydrolyzing compound (12) according to the method as described above.

Example A.13

A mixture of methyl 2-hydroxyacetate (0.2 mol) in THF (100 ml) was stirred on an ice bath. 2-Chloro-2-phenylacetyl chloride (0.132 mol) was added dropwise. The mixture was stirred overnight, poured out in water and then stirred for 20 minutes. The mixture was extracted with DEPE. The organic layer was separated, dried, filtered and the solvent was evaporated, yielding 30 g of benzeneacetic acid, α-chloro-, 2-methoxy-2-oxoethyl ester (intermediate 43).

Example A.14

A mixture of α-bromophenylacetic acid (0.1 mol) and thionyl chloride (0.1 mol) in DCM (100 ml) and DMF (5 drops) was stirred and refluxed for 1 hour. The solvent was evaporated. DCM (100 ml) was added three times. The solvent was evaporated. The residue was dissolved in DCM (100 ml). The mixture was cooled on ice. Methyl glycinate hydrochloride (0.1 mol) was added. The mixture was stirred at room temperature for 2 hours. A saturated NaHCO$_3$ solution was added. The mixture was stirred at room temperature over the weekend. The organic layer was separated, dried, filtered and the solvent was evaporated. The residue was triturated in DIPE. The precipitate was filtered off and dried, yielding 17.8 g of acetic acid, [(bromophenylacetyl)amino]-, methyl ester (intermediate 44).

Example A.15 a) A mixture of 1-benzyl-4-(p-bromophenyl)-4-piperidinol hydrochloride (0.23 mol) and Cu$_2$O (2 g) in NH$_4$OH (500 ml) was stirred at 180° C. for 12 hours. The mixture was cooled, extracted with DCM and washed with water. The organic layer was dried, filtered off and evaporated, yielding 60 g of 4-[1,2,3,6-tetrahydro-1-(phenylmethyl)-4-pyridinyl] benzenamine (intermediate 47).

b) 4'-(Trifluoromethyl)-[1,1'-biphenyl]-2-carbonyl chloride (0.12 mol) was added dropwise to a stirring mixture of intm. (47) (0.095 mol) in DCM (300 ml) and triethylamine (50 ml). The mixture was stirred overnight, poured out into water and then stirred for 30 minutes. The organic layer was separated, washed, dried, filtered and the solvent was evaporated. The residue was triturated in DIPE. The precipitate was filtered off and dried, yielding N-[4-[1,2,3,6-tetrahydro-1-(phenylmethyl)-4-pyridinyl]phenyl]-4'-(trifluoromethyl)-[1,1'-biphenyl]-2-carboxamide (intm. 48).

c) 1-Chloroethyl chloroformate (0.078 mol) was added dropwise to a stirring mixture of intermediate (48) (0.039 mol) in 1,2-dichloroethane (500 ml). The mixture was stirred for 30 minutes and then stirred and refluxed overnight. The solvent was evaporated. Methanol (500 ml) was added. The mixture was stirred and refluxed overnight. The solvent was evaporated. The residue was triturated in DIPE. The precipitate was filtered off and dried, yielding 20.8 g of N-[4-(1,2, 3,6-tetrahydro-4-pyridinyl)phenyl]-4'-(trifluoromethyl)-[1,1'-biphenyl]-2-carboxamide (intm. 49).

Example A.16 a) α-phenyl-1-(phenylmethyl)-4-piperidineacetic acid hydrobromide (1:1) (0.13 mol) was stirred in DCM (300 ml). Thionyl chloride (0.15 mol) was added. The reaction mixture was stirred and refluxed for 1 hour. More thionyl chloride (0.15 mol) was added and the reaction mixture was stirred and refluxed until complete dissolution (about 3 hours). The solvent was evaporated. The residue was dissolved in DCM (200 ml). Methanol (50 ml) was added. The mixture was stirred for 1 hour, neutralized with a NaHCO₃ solution. The separated organic layer was dried, filtered and the solvent was evaporated. The residue was dissolved in CH₃OH/DIPE and converted into the hydrochloric acid salt (1:1) with HCl/2-propanol. The formed precipitate was filtered off, dried, converted back into the free base with a NaHCO₃ solution and separated into enantiomers over Chiralcel OJ (eluent: methanol). The desired fractions were collected and the solvent was evaporated. Each of these fractions was taken up in CH₃OH/DIPE and converted into the hydrochloric acid salt with HCl/2-propanol, yielding 16.9 g (A)-α-phenyl-1-(phenylmethyl)-4-piperidineacetic acid methyl ester hydrochloride (1:1) (intermediate 50); mp. 189.9-190.0° C. and 12.2 g of (B)-α-phenyl-1-(phenylmethyl)-4-piperidineacetic acid, methyl ester hydrochloride (1:1) (intermediate 51); mp. 192.3-193°.

b) A mixture of intermediate (50) (0.047 mol) in methanol (250 ml) was hydrogenated at room temperature with palladium on carbon (10%, 2 g) as a catalyst (2 g). After uptake of hydrogen (1 equiv), the catalyst was filtered off and the filtrate was evaporated. The residue was triturated under 2-propanol, filtered off and dried, yielding 11.5 g (90%) of product. The filtrate was evaporated, yielding 1.1 g of (A)-α-phenyl-4-piperidineacetic acid, methyl ester hydrochloride (1:1) (intermediate 52).

c) A mixture of intermediate (52) (0.046 mol), 1-fluoro-4-nitrobenzene (0.05 mol) and sodium hydrogen carbonate (0.15 mol) in N,N-dimethylformamide (100 ml) was stirred for 4 hours at 50° C., then cooled and water was added. This mixture was extracted with CH₂Cl₂. The combined organic layers were washed with water, dried, filtered and the solvent evaporated. The residue was triturated under DIPE/hexane, filtered off and dried, yielding 14 g (86%) of (A)-1-(4-nitrophenyl)-α-phenyl-4-piperidineacetic acid, methyl ester (intermediate 53); mp. 105.2-105.3° C.

d) A mixture of intermediate (53) (0.025 mol) in hydrochloric acid (conc.) (100 ml) was stirred and refluxed for 16 hours, then cooled and the resulting precipitate was filtered off, washed with water (3×) and dried, yielding 8.77 g (91%) of (A)-1-(4-nitrophenyl)-α-phenyl-4-piperidineacetic acid hydrochloride (1:1) (intermediate 54); mp. 196.4-196.5° C.

e) A mixture of intermediate (54) (0.013 mol), glycine methyl ester hydrochloride (1:1) (98%) (0.026 mol), 1-hydroxybenzotriazole (0.015 mol) and 2,6-dimethylpyridine (0.052 mol) in CH₂Cl₂ (100 ml) was stirred. N,N'-methanetetraylbis-2-propanamine (0.026 mol) was added. The reaction mixture was stirred for 48 hours at room temperature. The mixture was washed with H₂O. The separated organic layer was dried, filtered and the solvent was evaporated. The residue was triturated under 2-propanol. The precipitate was filtered off and dried, yielding 4.37 g (80%) of (B)—N-[[1-(4-nitrophenyl)-4-piperidinyl]phenylacetyl]glycine methyl ester (intermediate 55); mp. 165.4-165.5° C.

f) A mixture of intermediate (55) (0.01 mol) in methanol (250 ml) was hydrogenated at 14° C. with palladium on carbon (10% 2 g) as a catalyst in the presence of thiophene (4%) (2 ml). After uptake of hydrogen (3 equiv.), the catalyst was filtered off and the filtrate was evaporated, yielding 3.81 g (quantitative yield) of (B)—N-[[1-(4-aminophenyl)-4-piperidinyl]phenylacetyl]glycine methyl ester (intermediate 56); $[\alpha]_D^{20}$=+31.37° (c=10.20 mg/5 ml in DMF).

B. Synthesis of the Final Compounds

Example B.1

A mixture of intermediate (2) (0.0117 mol) and Na₂CO₃ (0.0141 mol) in DMF (100 ml) was stirred at room temperature. A solution of intermediate (43) (0.0141 mol) in DMF (80 ml) was added dropwise. The mixture was stirred at room temperature for 20 hours. The solvent was evaporated. The residue was stirred in DCM (150 ml). The organic layer was washed with water, washed with a saturated NaHCO₃ solution and washed with water. The combined organic layer was dried, filtered and the solvent was evaporated. The residue was purified by column chromatography over silica gel (eluent: CH₂Cl₂/CH₃OH 99/1). The desired fractions were collected and the solvent was evaporated. The residue was stirred in DIPE (150 ml). The mixture was warmed up to reflux and 2-propanol (30 ml) and DCM (5 ml) was added. The mixture was stirred and refluxed until complete dissolution, then brought to room temperature. The mixture was stirred at room temperature for 60 hours. The precipitate was filtered off and dried in vacuo at 50° C., yielding 3.32 g of 2-methoxy-2-oxoethyl α-phenyl-4-[4-[[[4'-(trifluoromethyl)[1,1'-biphenyl]-2-yl]carbonyl]amino]phenyl]-1-piperazineacetate (compound 14, mp. 106° C.).

Compound (12, mp. 132° C.) was prepared analogously by reacting intermediate (2) with intermediate (44) using the method as described above.

Compound (13) was prepared analogously by reacting intermediate (14) with intermediate (44) using the method as described above.

Compound (15) was prepared analogously by reacting intermediate (10) with intermediate (44) using the method as described above.

Compound (16) was prepared analogously by reacting intermediate (14) with intermediate (43) using the method as described above.

Example B.2

A mixture of intermediate (20) (0.0041 mol), methyl glycinate hydrochloride (0.008 mol) and triethylamine (0.025 mol) in DCM (50 ml) was stirred and cooled at −25° C. PyBOP (0.005 mol) was added and the reaction mixture was stirred for 4 hours at a temperature of −25° C. The mixture was allowed to warm to room temperature. The residue was purified by column chromatography over silica gel (eluent: CH₂Cl₂/CH₃OH 100/0; 99/1). The product fractions were collected and the solvent was evaporated. The residue was triturated under DIPE, filtered off, washed with 2-propanol/H₂O (50/50; tree times) and dried, yielding 2.1 g of acetic acid, [[[1-[4-[[[4'-(1,1-dimethylethyl)[1,1'-biphenyl]-2-yl]carbonyl]amino]phenyl]-4-piperidinyl]phenylacetyl]amino]-, methyl ester hydrate (1:1) 2-propanolate (1:1) (compound 22).

Example B.3

A mixture of compound (22) (0.00072 mol) in concentrated HCl (20 ml) and dioxane (30 ml) was stirred and refluxed. The solvent was evaporated and 2-propanol was added and again the solvent was evaporated. The procedure was repeated, the reaction mixture was stirred and refluxed for 2 hours, cooled and extracted twice with DCM. The separated organic layers were dried, the solvent was evaporated and the residue was triturated under ethyl acetate, filtered off and dried, yielding 0.22 g of acetic acid, [[[1-[4-[[[4'-(1,1-dimethylethyl)[1,1'-biphenyl]-2-yl]carbonyl]amino]phenyl]-4-piperidinyl]phenylacetyl]amino]-hydrochloride (1:1) hydrate (1:1) (compound 25). Compound (23) was prepared analogously starting from compound (15) using the method as described above.

Example B.4

A mixture of intermediate (20) (0.0034 mol), ethylamine (0.07 mol; 2M in THF), N,N-dimethyl-4-pyridinamine (0.001 mol) and triethylamine (0.0034 mol) in DCM (100 ml) was stirred at room temperature. 1-Ethyl-3-(3-dimethylaminopropyl)carbodiimide hydrochloride (EDAP) (0.007 mol) was added and the mixture was stirred at room temperature for 6 hours, then washed with water. The separated organic layer was dried, filtered and the solvent was evaporated. The residue was purified by column chromatography over silica gel (eluent: $CH_2Cl_2/CH_3OH$, gradient: 100/0; 99/1; 98/2) yielding 4'-(1,1-dimethylethyl)-N-[4-[4-[2-(ethylamino)-2-oxo-1-phenylethyl]-1-piperidinyl]phenyl]-[1,1'-biphenyl]-2-carboxamide, and 4-fluoro-N-[4-(1-piperidinyl)phenyl]-benzamide (compound 24).

Example B.5

A mixture of intermediate (4) (0.00016 mol), PyBOP (0.00032 mol) and triethylamine (0.1 ml) in DCM (5 ml) was stirred for 30 minutes. Ethanolamine (0.0005 mol) was added and the reaction mixture was stirred overnight at 40° C. The reaction mixture was cooled. Water (2 ml) was added and the mixture was stirred for 15 minutes, then filtered through Extrelut™, and the desired compound was isolated by HPLC, yielding compound (1).

Example B.6

A mixture of intermediate (4) (0.000079 mol), 1,1'-carbonylbis-1H-imidazole (0.00024 mol) and triethylamine (0.00032 mol) in DCM (5 ml) was stirred for 30 minutes. This solution was added to (S)-leucine methyl ester hydrochloride (0.00016 mol). The reaction mixture was shaken for 20 hours at room temperature, then for 5 hours at 40° C. An additional amount of (S)-leucine methyl ester hydrochloride (0.00008 mol) in DCM (1 ml, p.a.) was added and the reaction mixture was shaken for 5 hours at 40° C. The reaction mixture was allowed to cool to room temperature, filtered and the filtrate was collected, then washed with water (2 ml). This mixture was filtered through Extrelut™ and the Extrelut™-filters were washed with DCM (2×3 ml). The filtrates were purified by HPLC (eluent: $CH_2Cl_2/CH_3OH$ 90/100). The product fractions were collected and the solvent was evaporated, yielding 0.041 g of pentanoic acid, 4-methyl-2-[[phenyl[4-[4-[[[4'-(trifluoromethyl)[1,1'-biphenyl]-2-yl]carbonyl] amino]phenyl]-1-piperazinyl]acetyl]amino]-, methyl ester, (2S)-(compound 26).

Example B.7

A mixture of intermediate (12) (0.000084 mol), PyBOP (0.00034 mol) and triethylamine (0.00034 mol) in DCM (5 ml) was stirred for 30 minutes at room temperature. This clear solution was added to (S)-leucine methyl ester hydrochloride (0.00017 mol). The reaction mixture was shaken for 24 hours at 40° C. The reaction mixture was filtered and the filter residue was washed once with 4 ml of DCM. To the filtrate, water (2 ml) was added and the mixture was stirred for 30 minutes. The mixture was filtered through Extrelut™ and the filter residue was rinsed 2× with DCM (3 ml). The filtrate was evaporated and the residue was purified by HPLC (Waters column, with Xterra MS C18; eluent: [(0.5% $NH_4OAc$ in $H_2O$)/$CH_3CN$ 90/10)]/$CH_3OH$/$CH_3CN$ (0 min) 75/25/0, (10 minutes) 0/50/50, (16 minutes) 0/0/100, (18.10-20.00 minutes) 75/25/0), yielding pentanoic acid, 4-methyl-2-[[phenyl [4-[4-[[[4'-(trifluoromethyl)[1,1'-biphenyl]-2-yl]carbonyl] amino]phenyl]-1-piperidinyl]acetyl]amino]-, methyl ester, (2S)-(compound 64).

Example B.8

Ethyl 2-bromopropionate (0.0001 mol) was added to a mixture of intermediate (12) (0.000084 mol) and tri-n-butylthiourea (TBTU) (0.000168 mol) in DIPEA (4 ml). The reaction mixture was shaken for 2 hours at 70° C. The reaction mixture was cooled to room temperature, filtered and the filtrate was evaporated. The residue was dissolved in DCM (4 ml), then washed with water (2 ml). The mixture was filtered through Extrelut™ and the filter residue was washed with DCM (2×3 ml). The filtrate was evaporated. The residue was purified by HPLC (Waters column, with Xterra MS C18; eluent: [(0.5% $NH_4OAc$ in $H_2O$)/$CH_3CN$ 90/10)]/$CH_3CN$ (0 min) 85/15, (10 min) 10/90, (16 min) 0/100, (18.10-20.00 min) 85/15), yielding 1-piperidineacetic acid, α-phenyl-4-[4-[[[4'-(trifluoromethyl)[1,1'-biphenyl]-2-yl]carbonyl]amino] phenyl]-, 2-ethoxy-1-methyl-2-oxoethyl ester (compound 111).

Example B.9

2-Bromoethanol (1.2 equiv, 0.00010 mol) was added to a mixture of intermediate (24) (0.000084 mol) in DMF (5 ml) and CsCO3 (0.00018 mol) and the reaction mixture was stirred for 3 hours at 70° C. The solvent was evaporated. The residue was partitioned between water and DCM. The extract's solvent was evaporated. The residue was purified by HPLC (Waters column, with Xterra MS C18; eluent: [(0.5% $NH_4OAc$ in $H_2O$)/$CH_3CN$ 90/10)]/$CH_3CN$ (0 minutes) 85/15, (10 minutes) 10/90, (16 minutes) 0/100, (18.10-20.00 minutes) 85/15). The product fractions were collected and the organic solvent was evaporated. The aqueous concentrates were extracted and the extract's solvent was evaporated, yielding 4-piperidineacetic acid, α-phenyl-1-[4-[[[4'-(trifluoromethyl)[1,1'-biphenyl]-2-yl]carbonyl]amino]phenyl]-, 2-hydroxyethyl ester (compound 134).

Example B.10

A mixture of intermediate (40) (0.00014 mol), intermediate (44) (0.00016 mol) and $Na_2CO_3$ (0.00016 mol) in DMF (5 ml) was stirred overnight at 60° C. The solvent was evaporated. The residue was dissolved in DCM (10 ml), washed with water (2 ml), filtered through Extrelut™ and the filtrate was evaporated. The residue was purified by HPLC. The product fractions were collected and the solvent was evaporated, yielding 0.052 g of acetic acid, [[[4-[4-[((1,1'-biphenyl]-2-ylcarbonyl)amino]phenyl]-1-piperidinyl]pheny lacetyl]amino]-, methyl ester (compound 17). Compound (142) was prepared analogously by reacting intermediate (44) with intermediate (49) using the method as described above.

Example B.11

A mixture of intermediate (24) (0.000084 mol), PyBOP (0.00017 mol) and triethylamine (0.5 ml) in DCM (5 ml) was stirred for 60 minutes at room temperature. Methyl hydroxyacetate (0.0001 mol) was added and the reaction mixture was stirred for 3 hours at 40° C., then over the weekend at room temperature. Water (2 ml) was added. The mixture was stirred for 15 minutes, then filtered through Extrelut™ and the organic filtrate was evaporated. The residue was purified by HPLC. The product fractions were collected and the solvent was evaporated, yielding 4-piperidineacetic acid, α-phenyl-1-[4-[[[4'-(trifluoromethyl)[1,1'-biphenyl]-2-yl]carbonyl]amino]-phenyl]-, 2-methoxy-2-oxoethyl ester (compound 20).

Example B.12

A mixture of compound (97) (0.00081 mol), DCM (15 ml) and trifluoroacetic acid (5 ml) was stirred at room temperature for 2 hours. The solvent was evaporated. DCM was added and evaporated (three times). The residue was stirred in DIPE. The precipitate was filtered off, dried and purified by high performance liquid chromatography over hyperprep C18 BDS (eluent: (0.5% NH$_4$OAc in H$_2$O/CH$_3$CN 90/10)/CH$_3$OH/CH$_3$CN 45/35/20; 8/47/45; 0/0/100). The desired fractions were collected and the solvent was evaporated. The residue was stirred in DIPE. The precipitate was filtered off, washed with DIPE and dried, yielding compound (143).

Example B.13

4'-(1,1-Dimethylethyl)-[1,1'-biphenyl]-2-carboxylic acid, (0.011 mol) was stirred in DCM (100 ml). Thionyl chloride (0.022 mol) was added. DMF (3 drops) was added and the reaction mixture was stirred and refluxed for one hour. The reaction mixture was cooled and the solvent was evaporated. DCM (100 ml) was added and the solvent was evaporated again. The residue was dissolved in DCM (50 ml) and this solution was added to a solution of intermediate (56) (0.0097 mol) in DCM (50 ml). The mixture was stirred. Sodium hydrogen carbonate (saturated aqueous solution) (50 ml) was added and the mixture was stirred for 2 hours at room temperature. The layers were separated. The organic layer was dried, filtered and the solvent evaporated. The residue was purified by column chromatography over silica gel (eluent: CH$_2$Cl$_2$/CH$_3$OH 98/2). The product fractions were collected and the solvent was evaporated. The residue was crystallized from 2-propanol/DIPE, filtered off and dried (vacuum, 50° C.), yielding 5.27 g of product. This fraction was dried (vacuum, 80° C., over the weekend), yielding 4.95 g of (B)—N-[[1-[4-[[[4'-(1,1-dimethylethyl)[1,1'-biphenyl]-2-yl]carbonyl]amino]phenyl]-4-piperidinyl]phenylacetyl]-glycine methyl ester (compound 145); mp. 119.9-120° C.

Table F-1 lists the compounds that were prepared according to one of the above Examples. The following abbreviations were used in the tables: .C$_3$H$_8$O stands for the 2-propanolate salt.

TABLE F-1

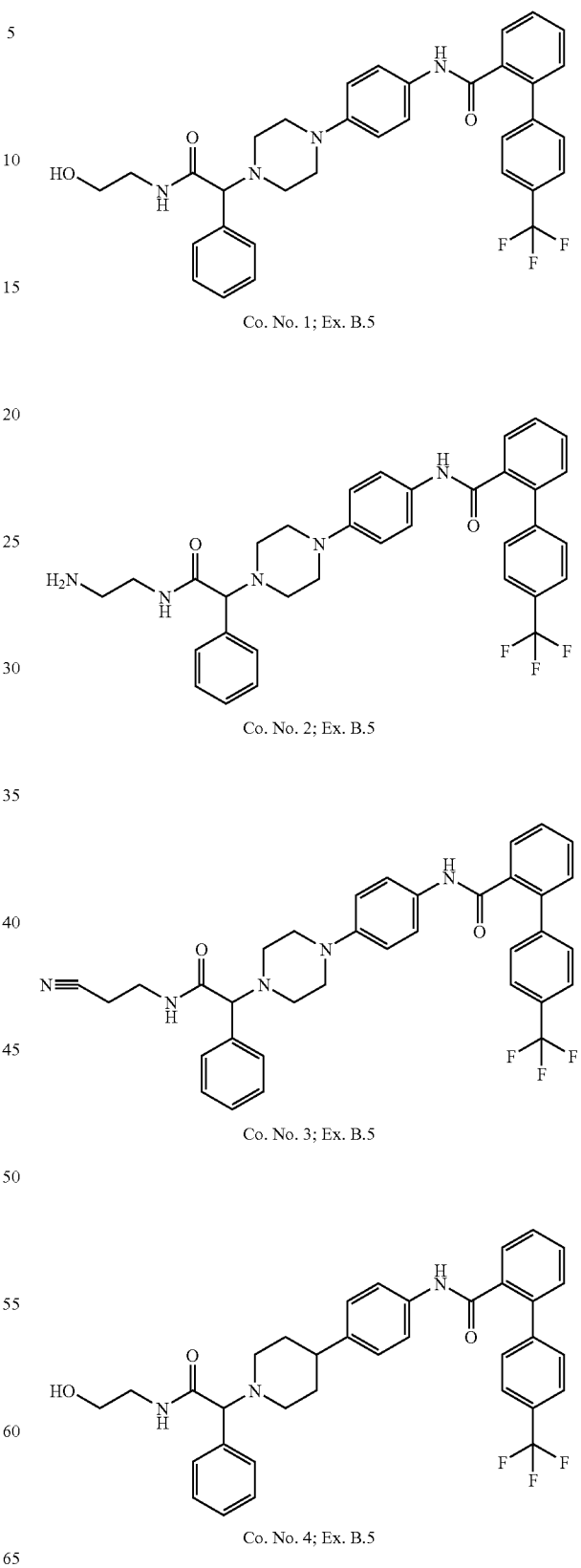

TABLE F-1-continued
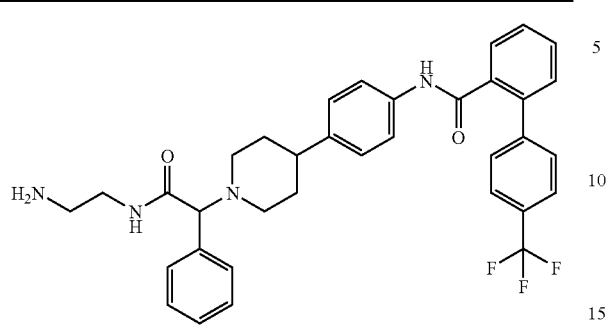
Co. No. 5; Ex. B.5
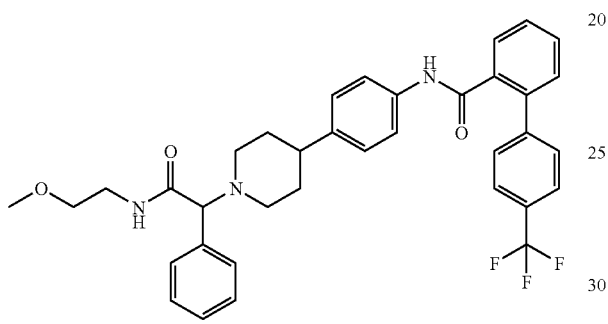
; Co. No. 6; Ex. B.5
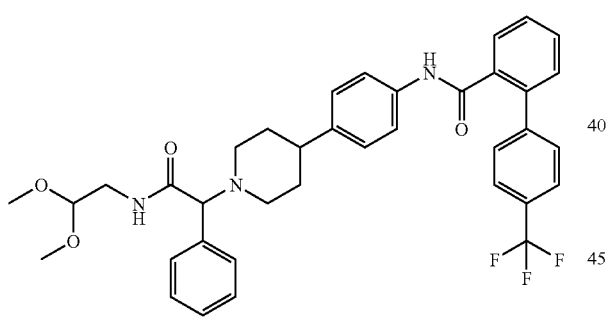
Co. No. 7; Ex. B.5
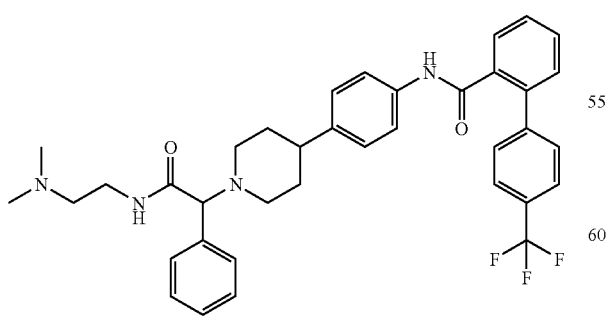
Co. No. 8; Ex. B.5
TABLE F-1-continued
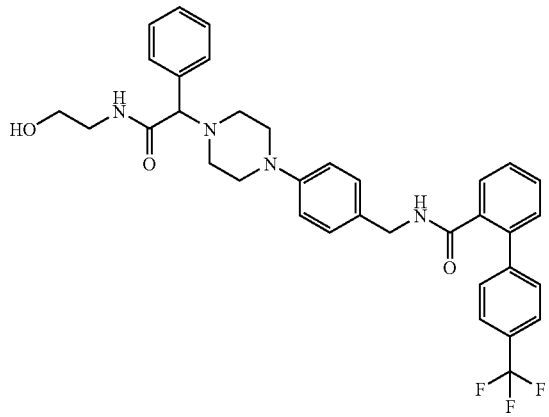
Co. No. 9; Ex. B.5
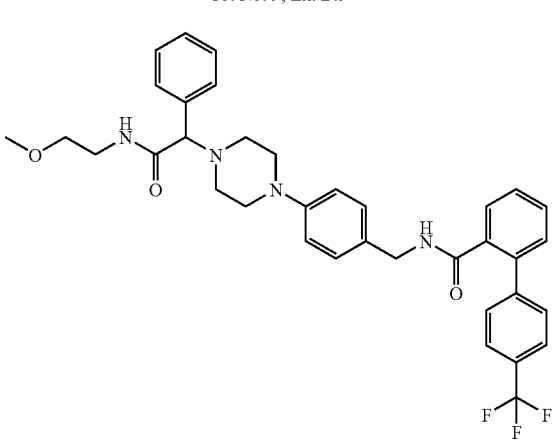
Co. No. 10; Ex. B.5
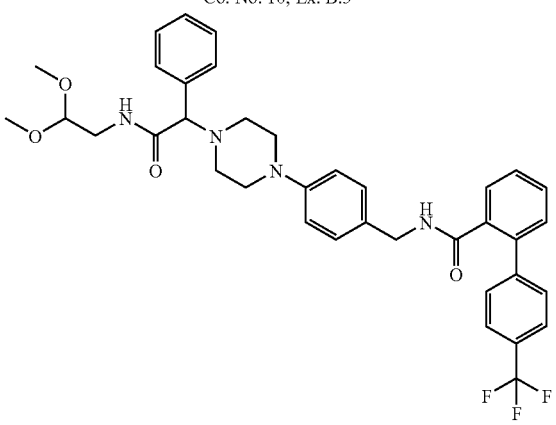
Co. No. 11; Ex. B.5
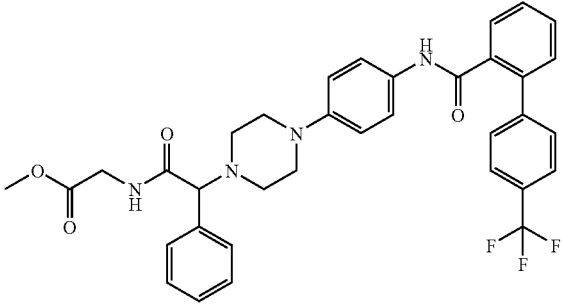
Co. No. 12; Ex. B.1

TABLE F-1-continued
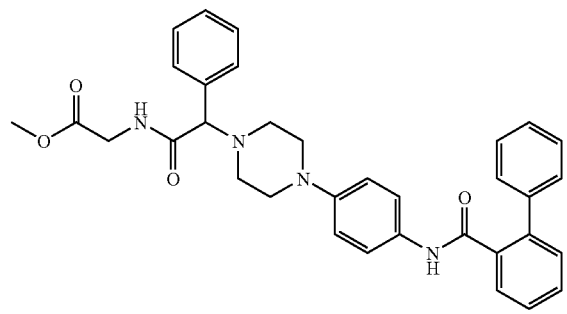
Co. No. 13; Ex. B.1
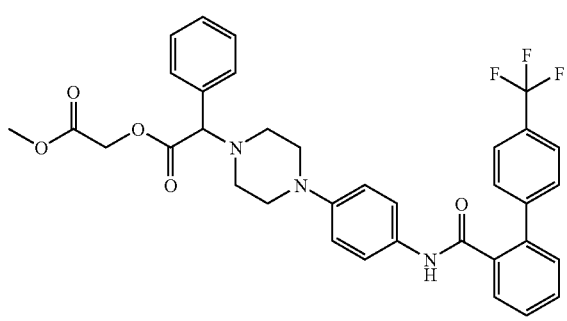
Co. No. 14; Ex. B.2
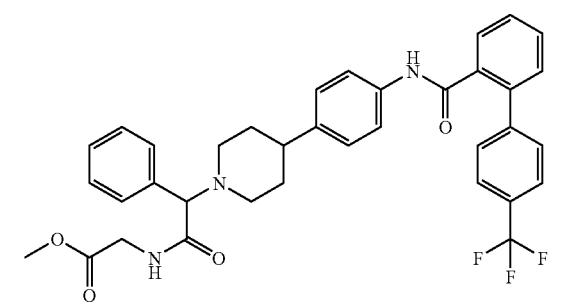
Co. No. 15; Ex. B.5
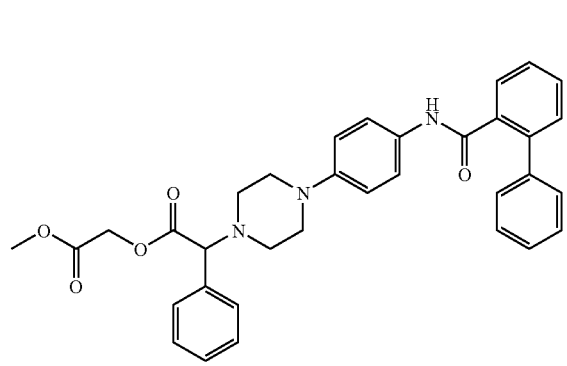
•2 HCl•H₂O•C₃H₈O; Co. No. 16; Ex. B.2
TABLE F-1-continued
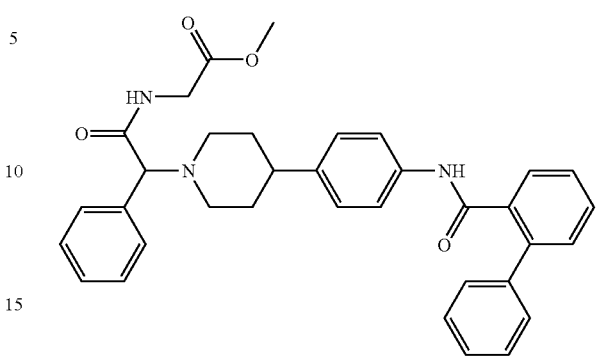
Co. No. 17; Ex. B.10
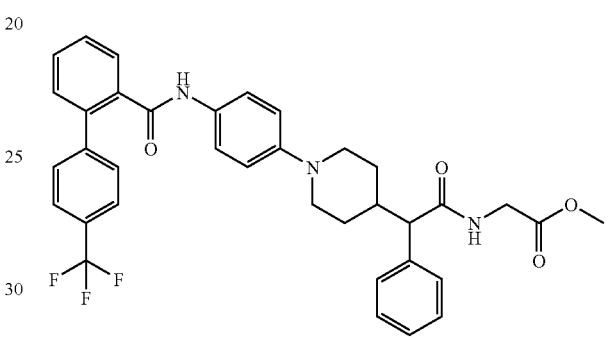
Co. No. 18; Ex. B.7
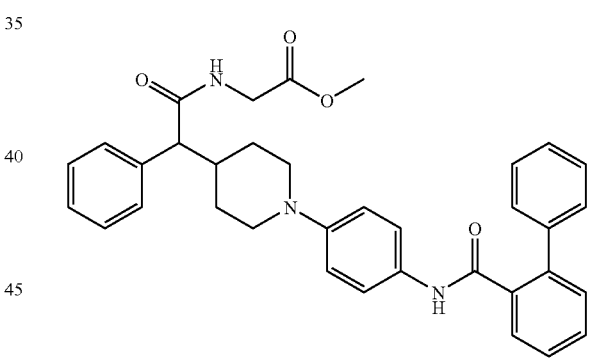
Co. No. 19; Ex. B.7
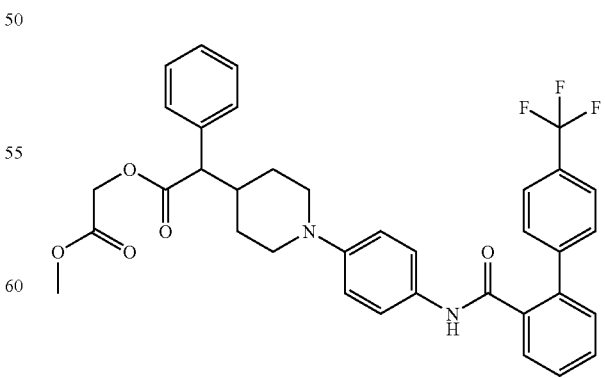
Co. No. 20; Ex. B.11

TABLE F-1-continued
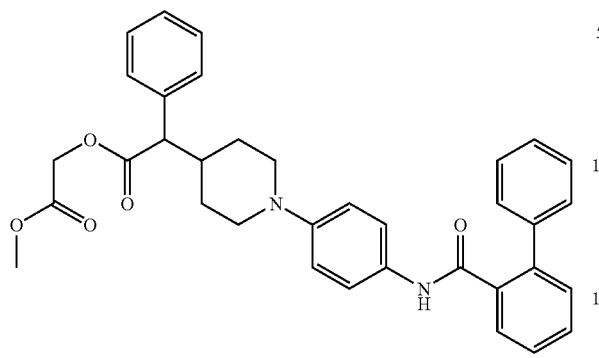
Co. No. 21; Ex. B.11
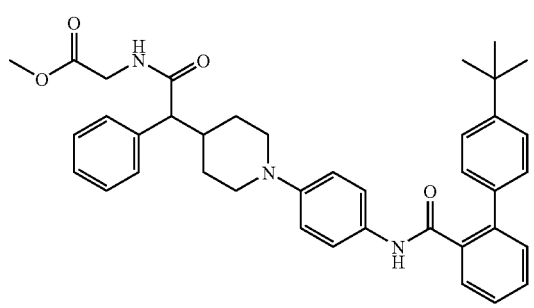
•H₂O•C₃H₈O; Co. No. 22; Ex. B.2
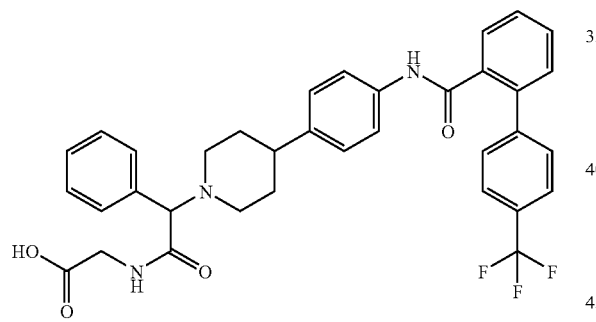
•H₂O; Co. No. 23; Ex. B.3
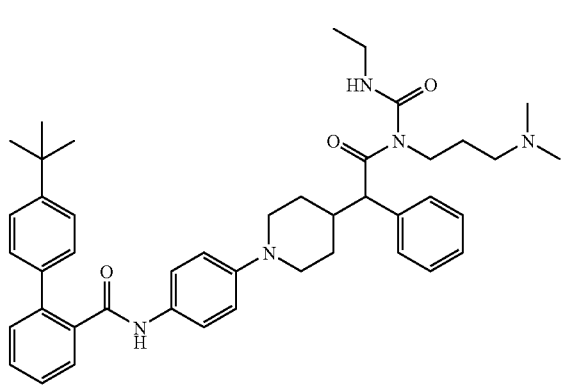
Co. No. 24; Ex. B.4
TABLE F-1-continued
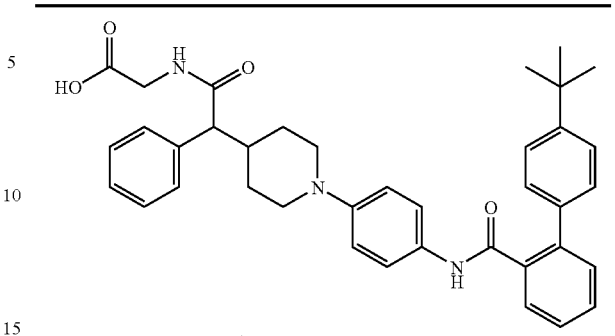
•HCl•H₂O; Co. No. 25; Ex. B.3
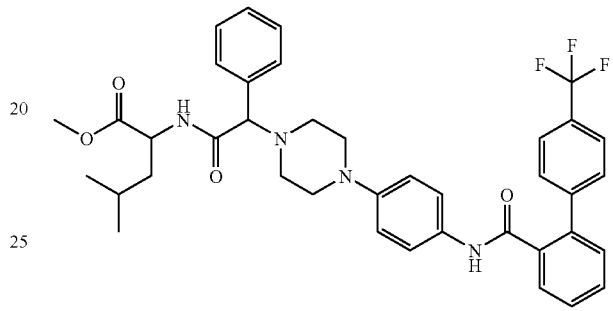
(S) Co. No. 26; Ex. B.6
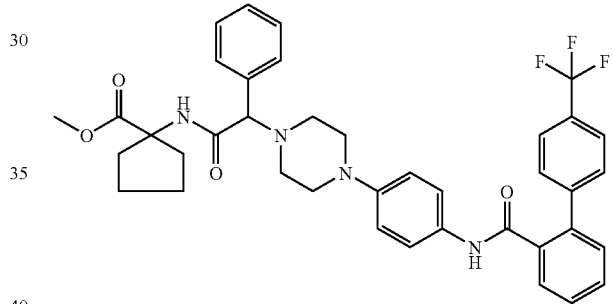
Co. No. 27; Ex. B.6
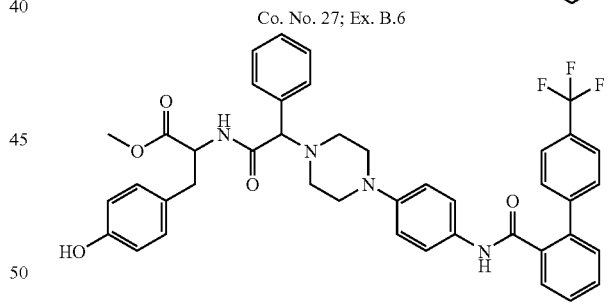
(S); Co. No. 28; Ex. B.6
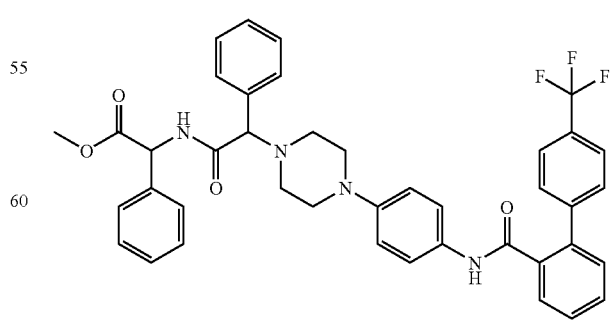
(R); Co. No. 29; Ex. B.6

TABLE F-1-continued
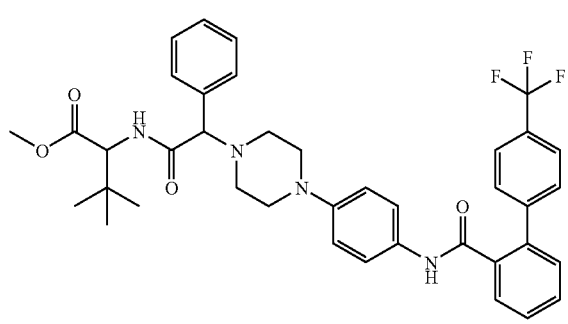
(S); Co. No. 30; Ex. B.6
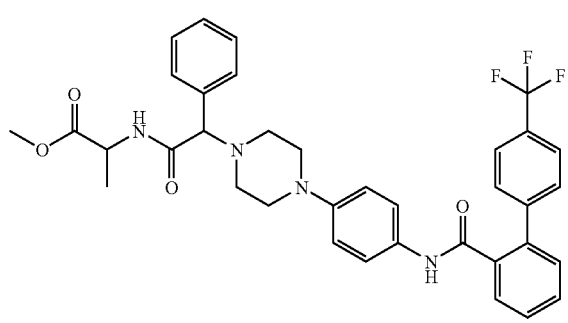
Co. No. 31; Ex. B.6
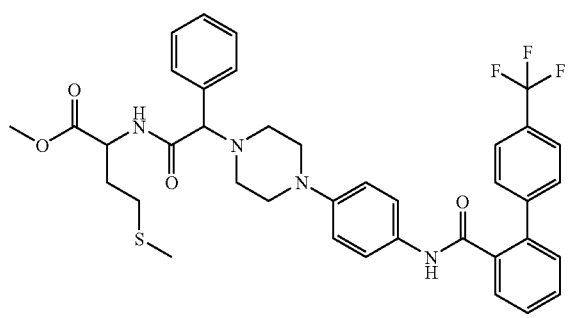
(S); Co. No. 32; Ex. B.6
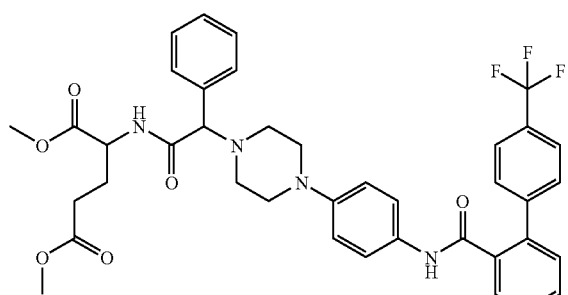
(S); Co. No. 33; Ex. B.6
TABLE F-1-continued
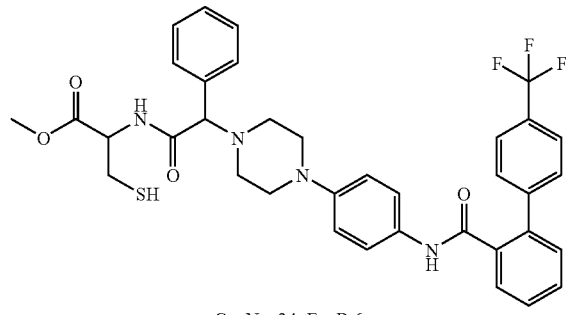
Co. No. 34; Ex. B.6
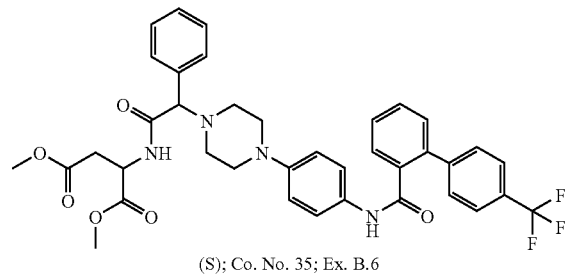
(S); Co. No. 35; Ex. B.6
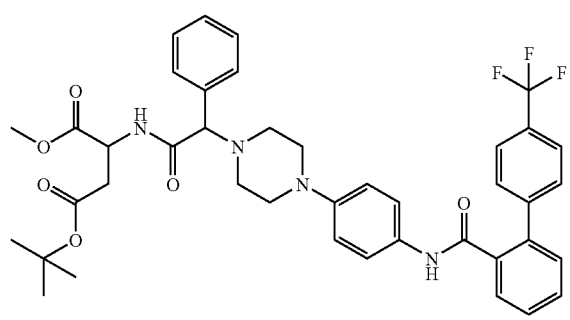
Co. No. 36; Ex. B.6
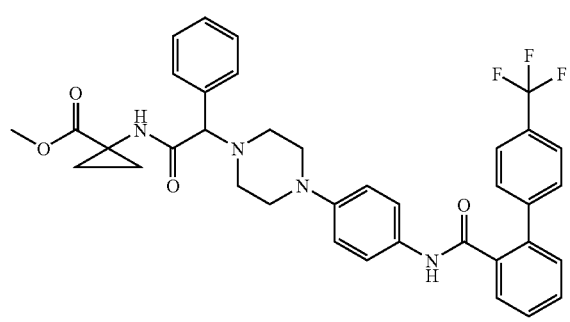
Co. No. 37; Ex. B.6
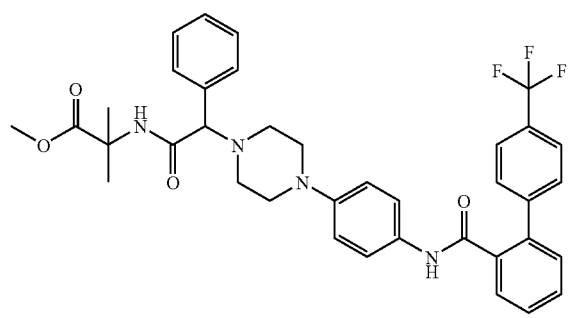
Co. No. 38; Ex. B.6

TABLE F-1-continued
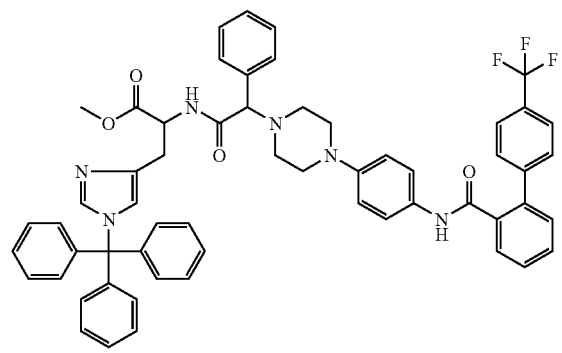
Co. No. 39; Ex. B.6
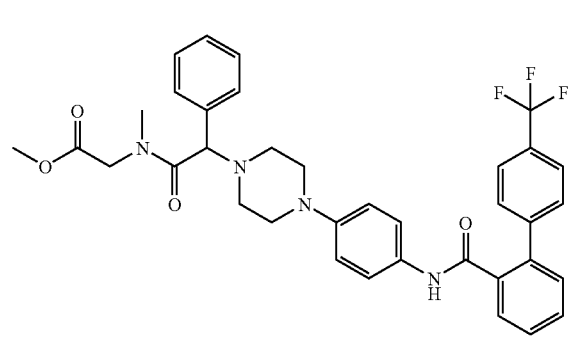
Co. No. 40; Ex. B.6
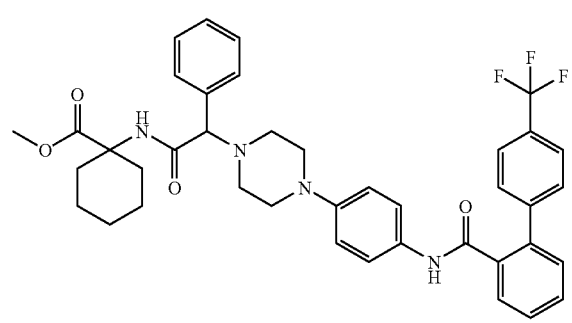
Co. No. 41; Ex. B.6
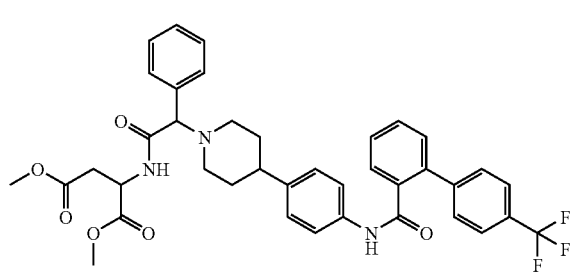
(S); Co. No. 42; Ex. B.7
TABLE F-1-continued
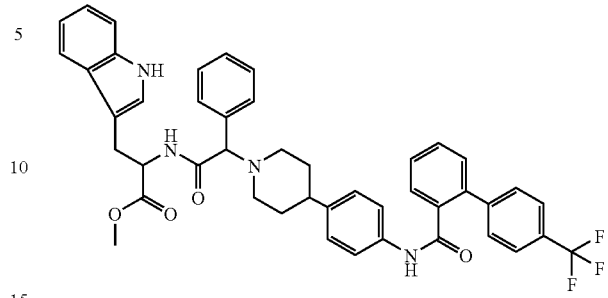
Co. No. 43; Ex. B.7
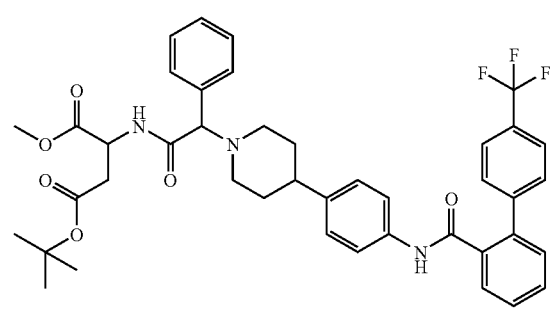
Co. No. 44; Ex. B.7
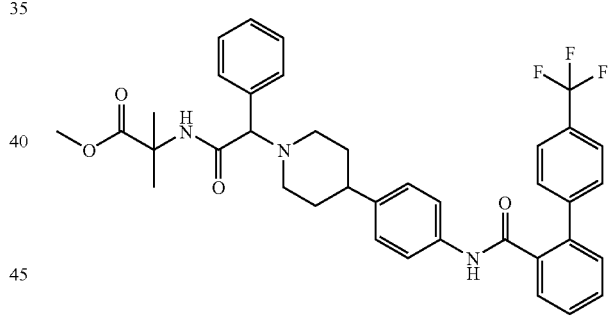
Co. No. 45; Ex. B.7
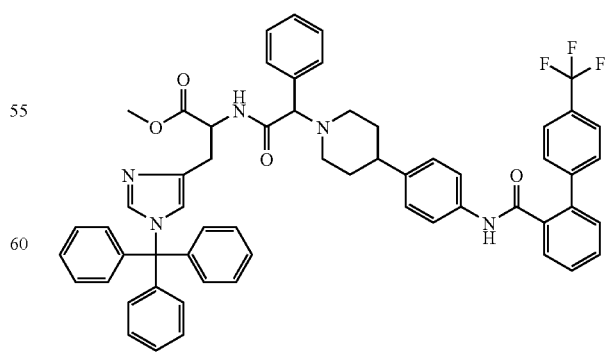
Co. No. 46; Ex. B.7

TABLE F-1-continued
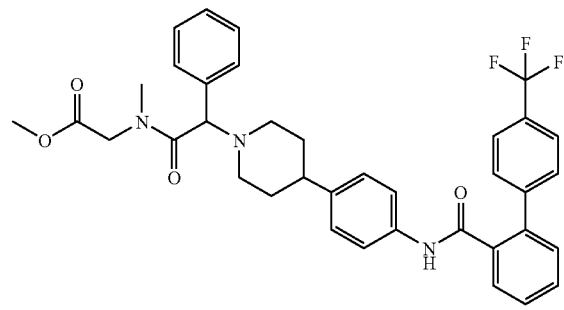
Co. No. 47; Ex. B.7
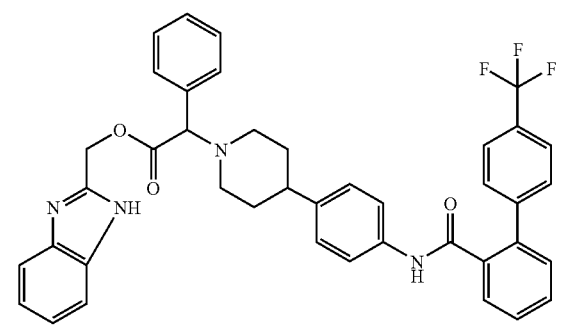
Co. No. 48; Ex. B.8
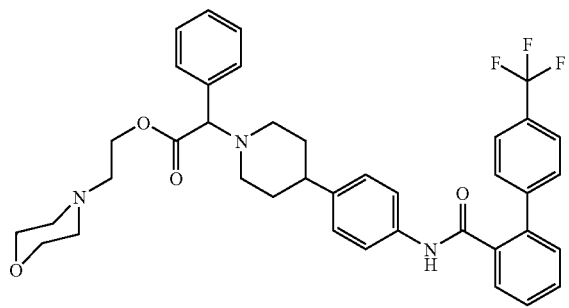
Co. No. 49; Ex. B.8
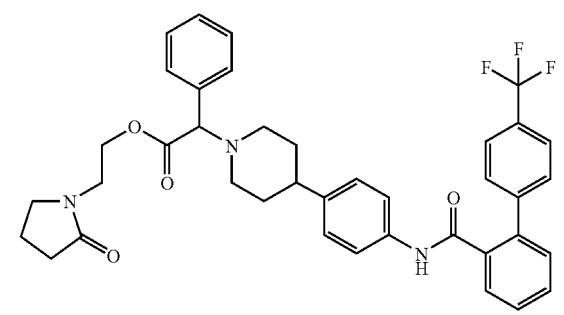
Co. No. 50; Ex. B.8
TABLE F-1-continued
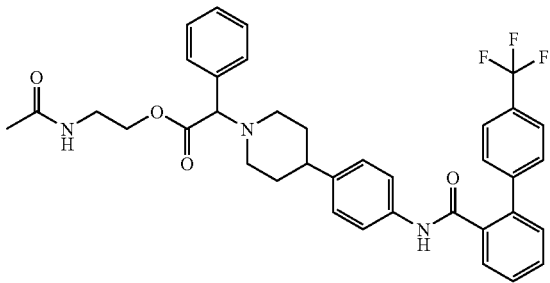
Co. No. 51; Ex. B.8
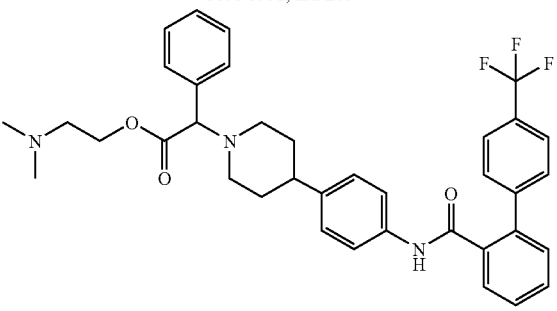
Co. No. 52; Ex. B.8
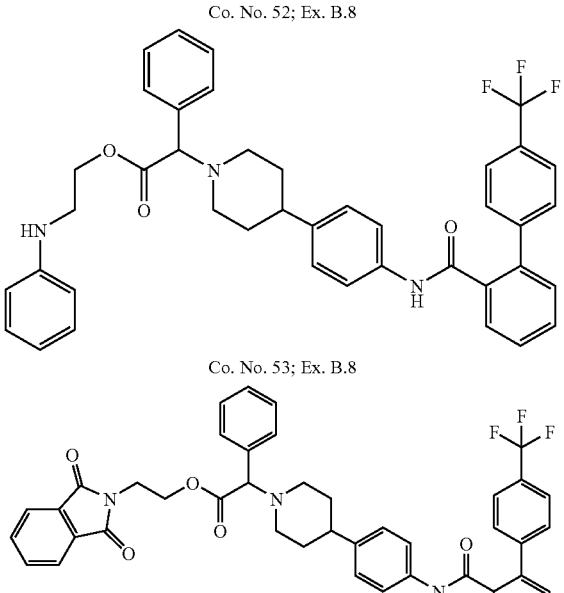
Co. No. 53; Ex. B.8
Co. No. 54; Ex. B.8
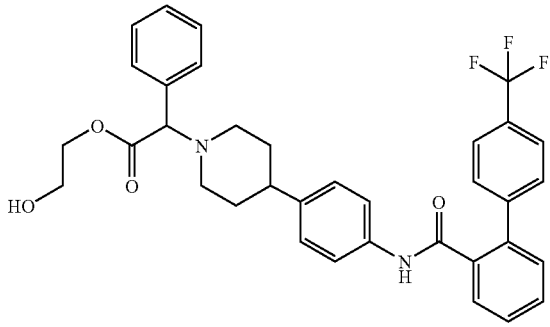
Co. No. 55; Ex. B.8

TABLE F-1-continued
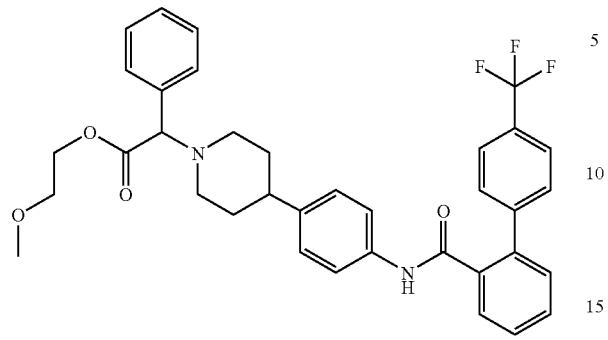
Co. No. 56; Ex. B.8
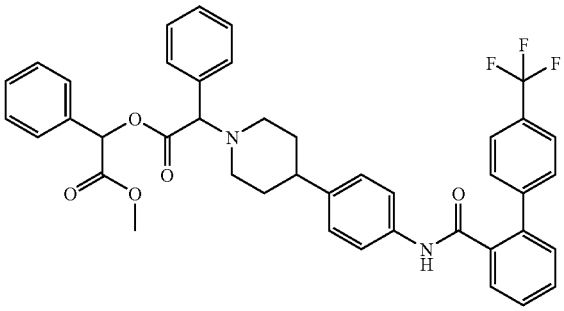
Co. No. 60; Ex. B.8
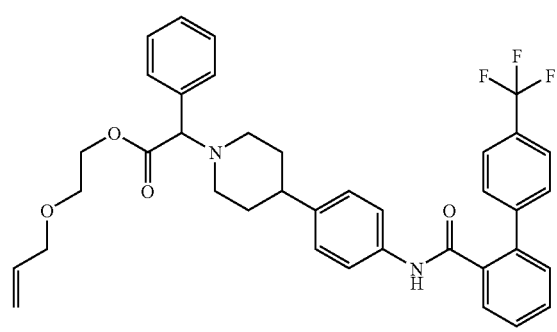
Co. No. 57; Ex. B.8
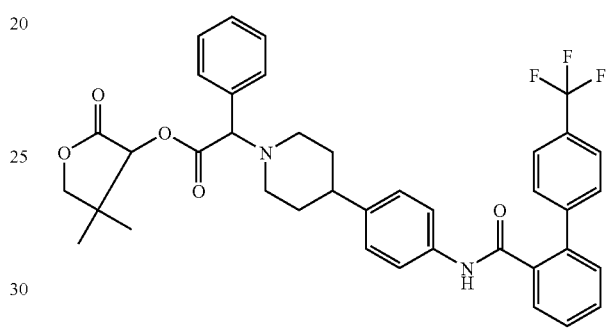
(R); Co. No. 61; Ex. B.8
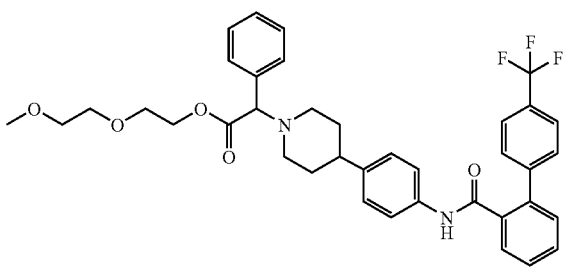
Co. No. 58; Ex. B.8
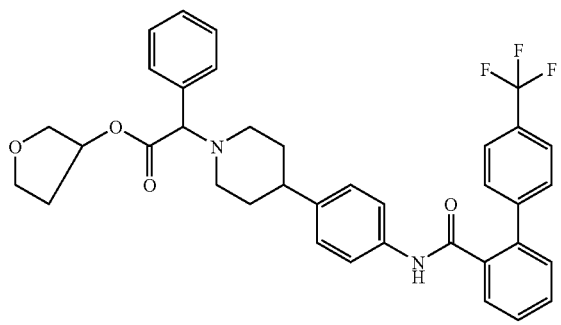
Co. No. 62; Ex. B.8
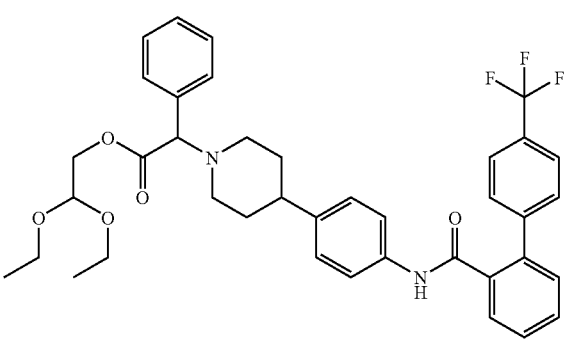
Co. No. 59; Ex. B.8
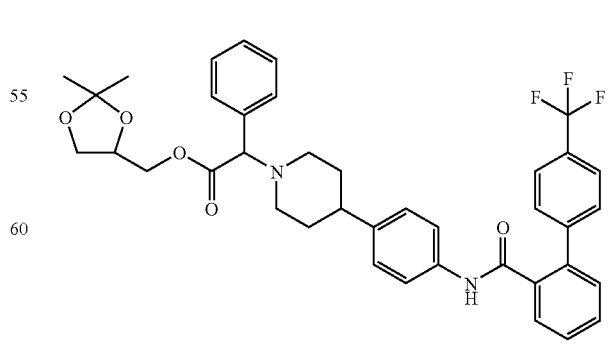
Co. No. 63; Ex. B.8

TABLE F-1-continued
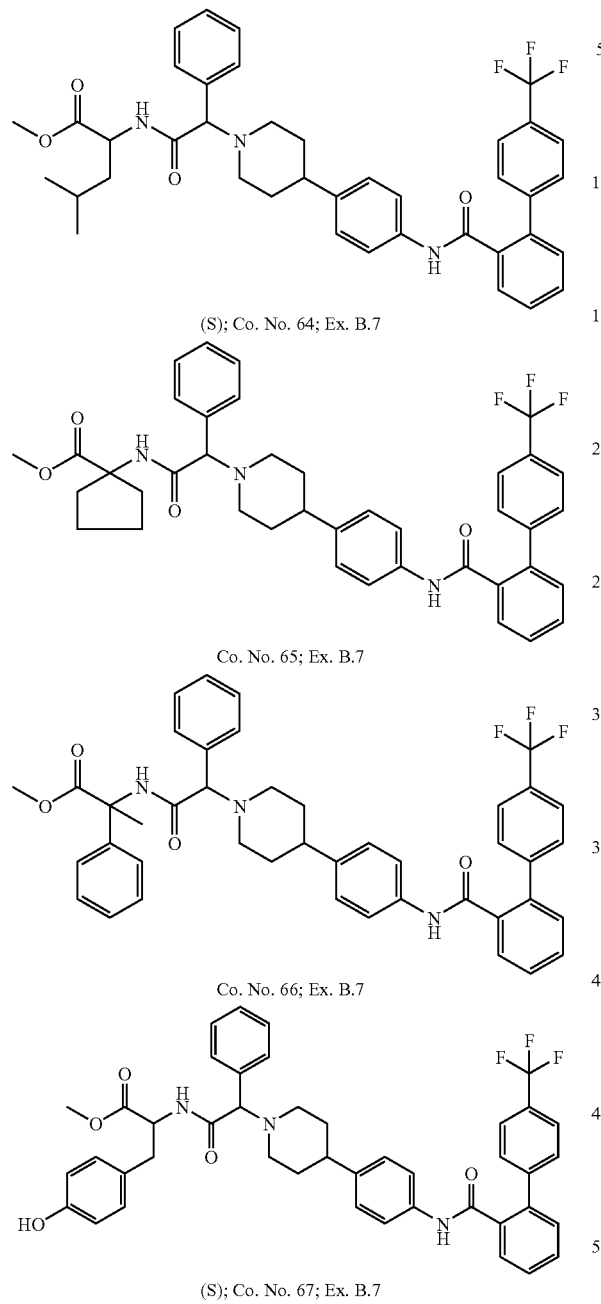
(S); Co. No. 64; Ex. B.7
Co. No. 65; Ex. B.7
Co. No. 66; Ex. B.7
(S); Co. No. 67; Ex. B.7
(R); Co. No. 68; Ex. B.7
TABLE F-1-continued
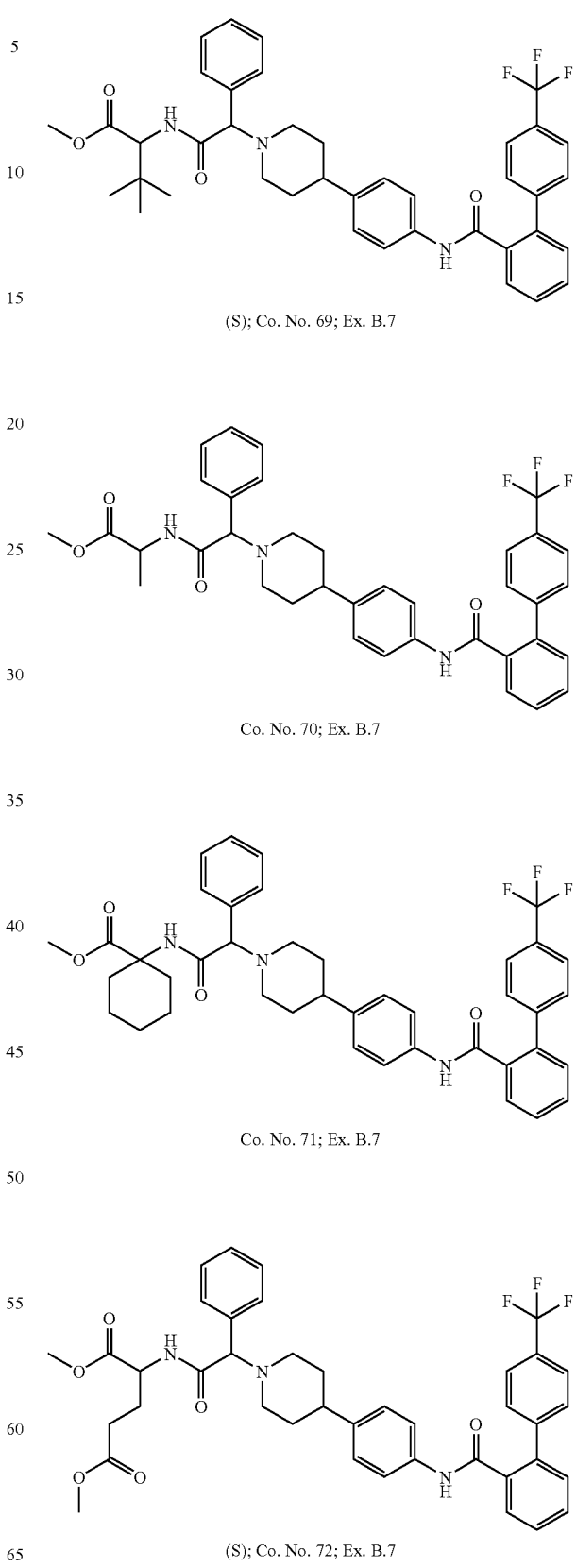
(S); Co. No. 69; Ex. B.7
Co. No. 70; Ex. B.7
Co. No. 71; Ex. B.7
(S); Co. No. 72; Ex. B.7

TABLE F-1-continued
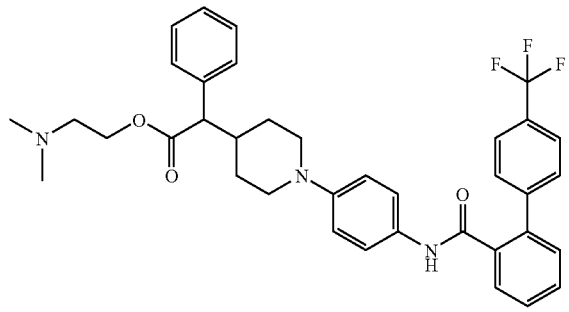
Co. No. 73; Ex. B.8
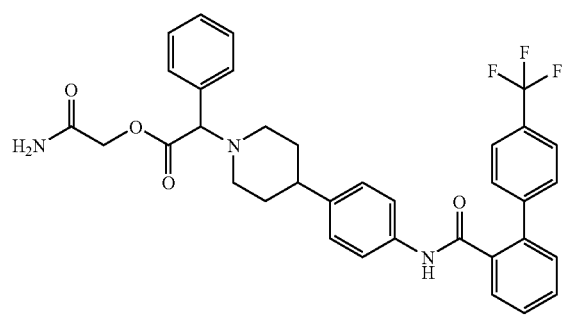
Co. No. 74; Ex. B.8
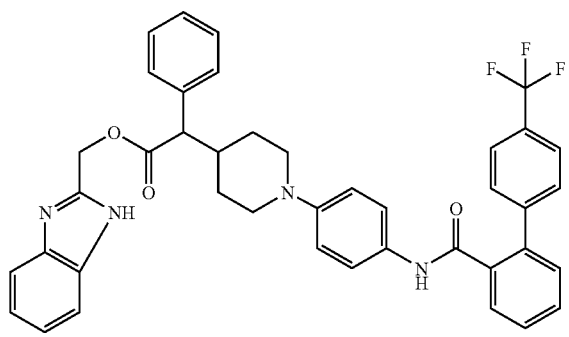
Co. No. 75; Ex. B.8
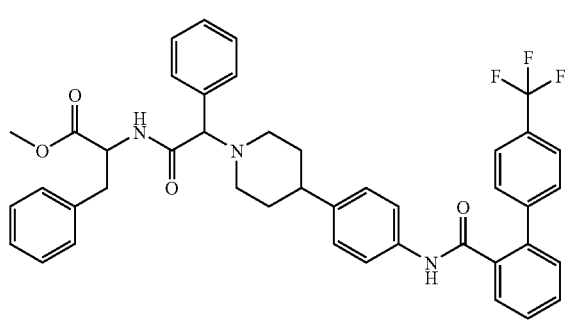
(S); Co. No. 76; Ex. B.7
TABLE F-1-continued
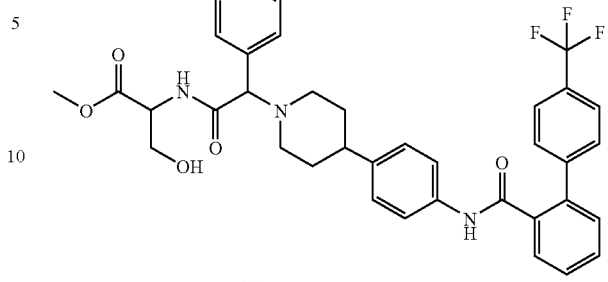
(S); Co. No. 77; Ex. B.7
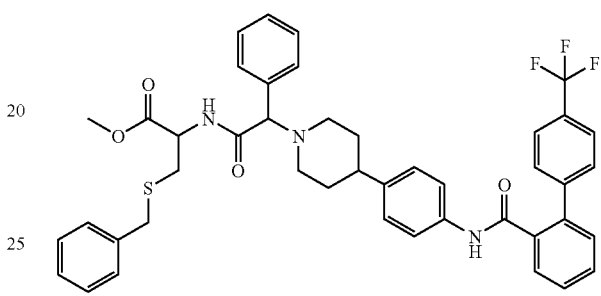
(R); Co. No. 78; Ex. B.7
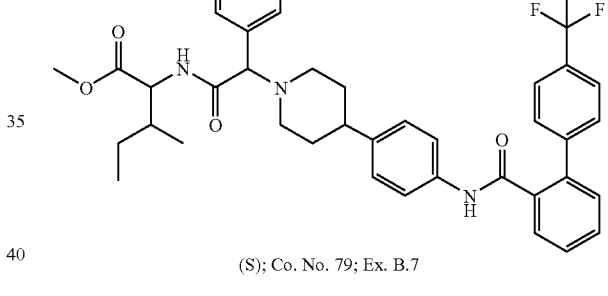
(S); Co. No. 79; Ex. B.7
Co. No. 80; Ex. B.7
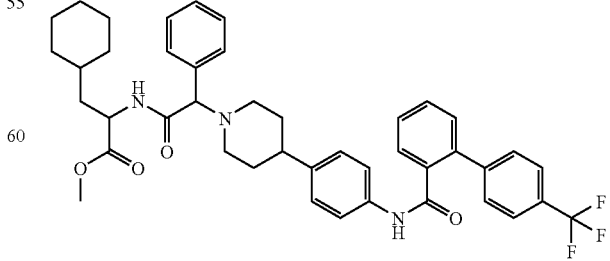
Co. No. 81; Ex. B.7

TABLE F-1-continued
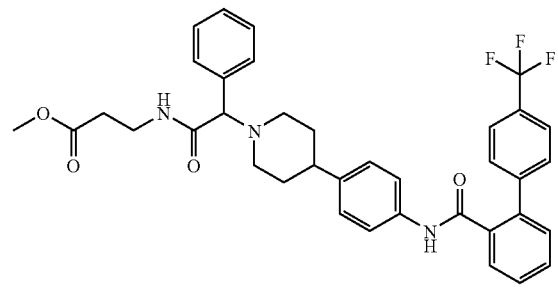
Co. No. 82; Ex. B.7
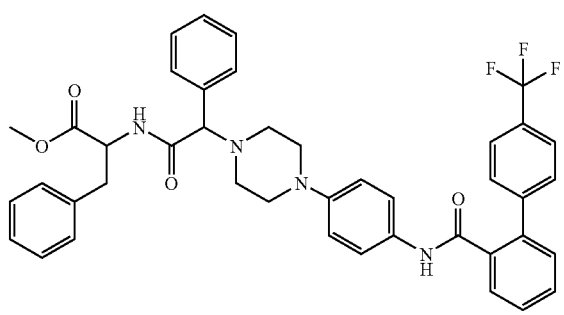
(S); Co. No. 83; Ex. B.7
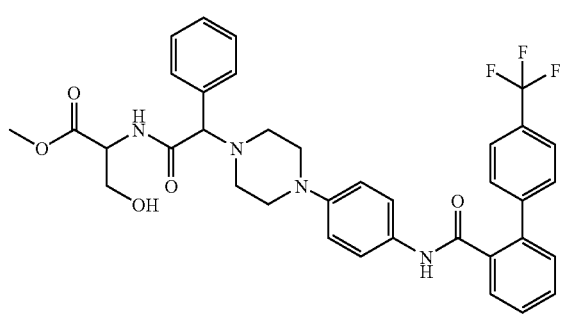
(S); Co. No. 84; Ex. B.7
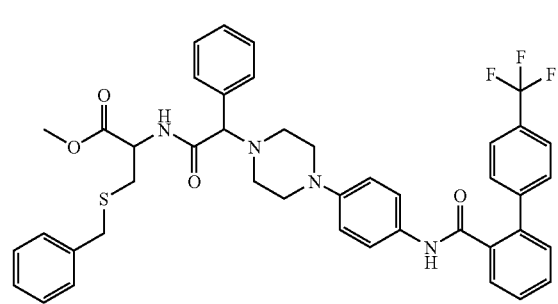
(R); Co. No. 85; Ex. B.7
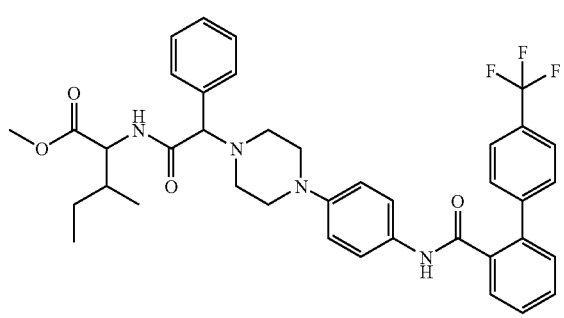
(S); Co. No. 86; Ex. B.7
TABLE F-1-continued
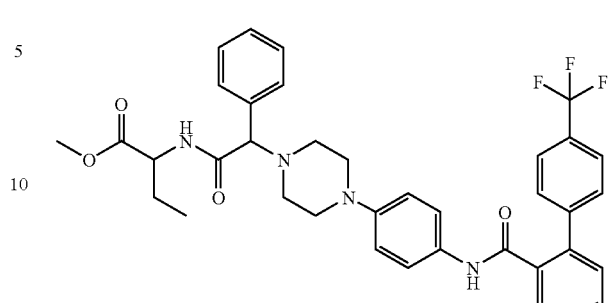
Co. No. 87; Ex. B.7
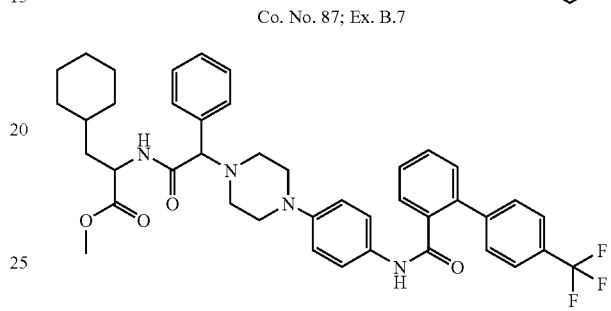
Co. No. 88; Ex. B.7
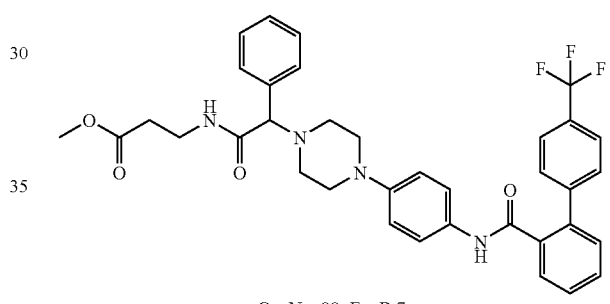
Co. No. 89; Ex. B.7
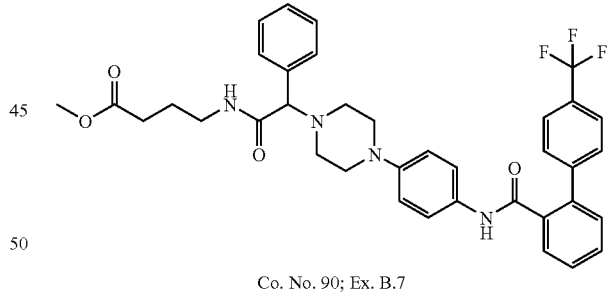
Co. No. 90; Ex. B.7
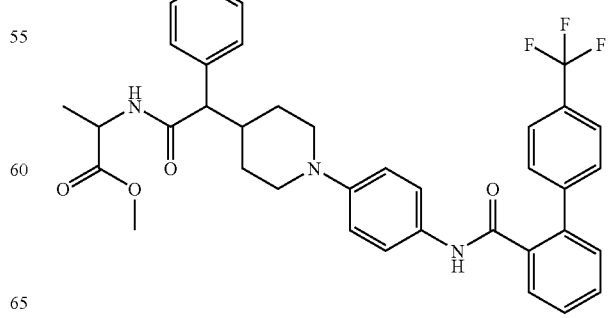
Co. No. 91; Ex. B.7

TABLE F-1-continued
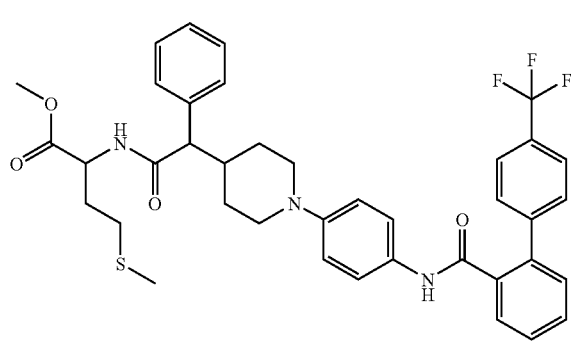
(S); Co. No. 92; Ex. B.7
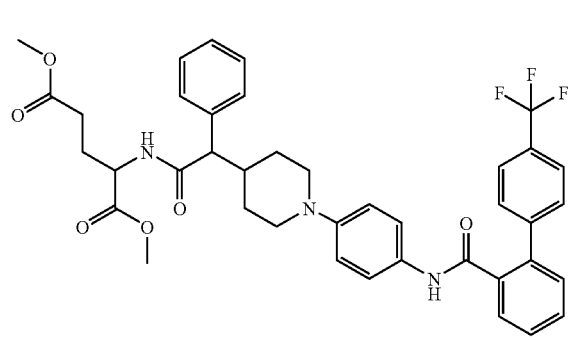
(S); Co. No. 93; Ex. B.7
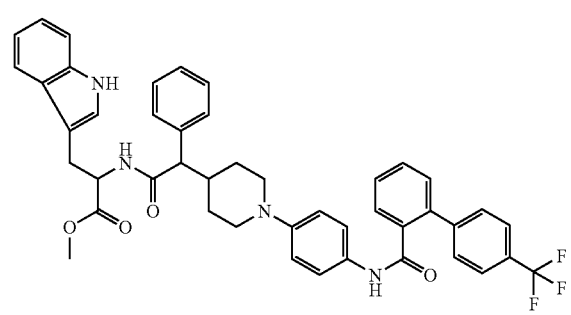
Co. No. 94; Ex. B.7
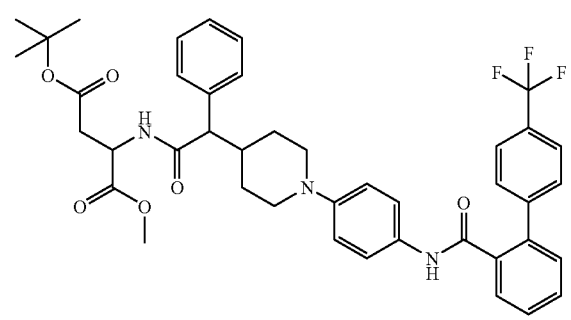
Co. No. 95; Ex. B.7
TABLE F-1-continued
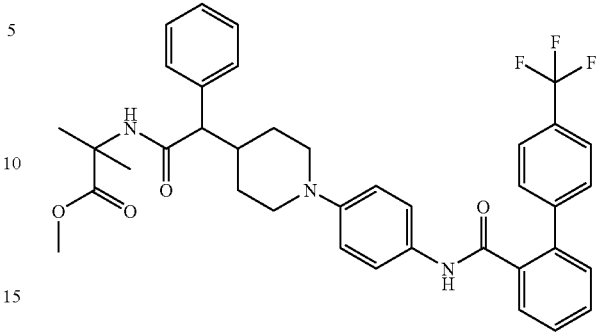
Co. No. 96; Ex. B.7
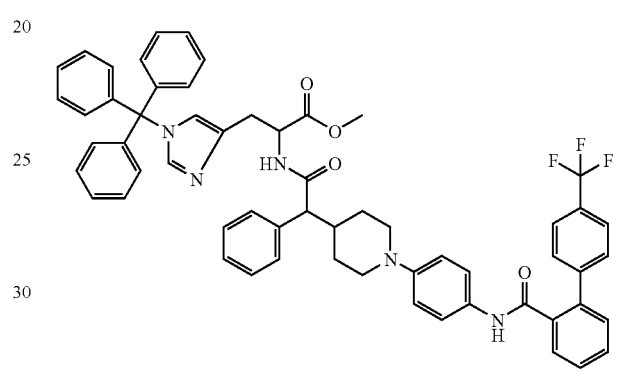
Co. No. 97; Ex. B.7
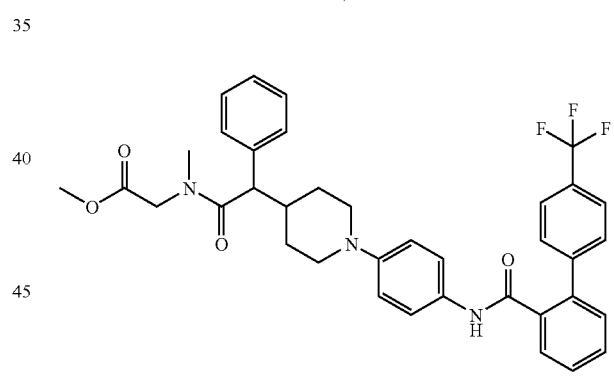
Co. No. 98; Ex. B.7
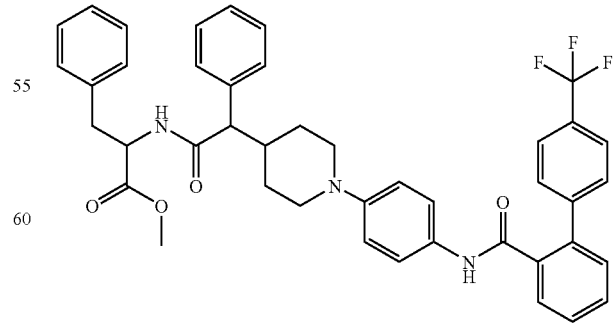
(S); Co. No. 99; Ex. B.7

TABLE F-1-continued
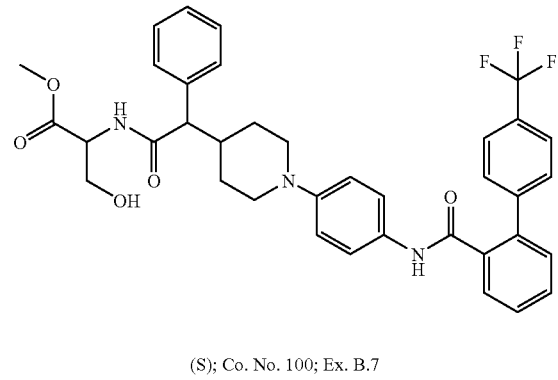
(S); Co. No. 100; Ex. B.7
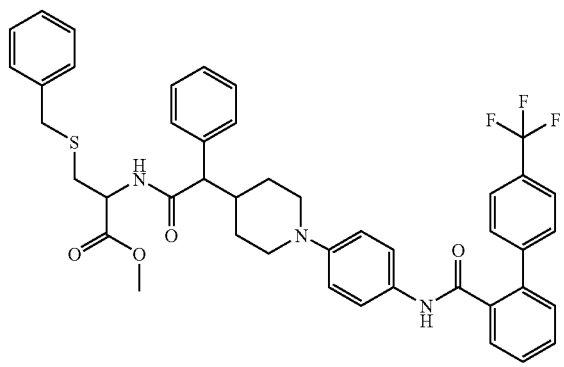
(R); Co. No. 101; Ex. B.7
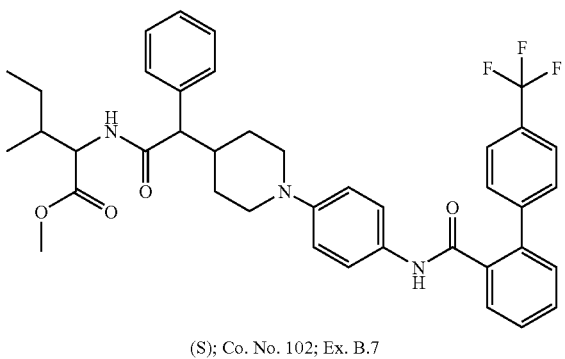
(S); Co. No. 102; Ex. B.7
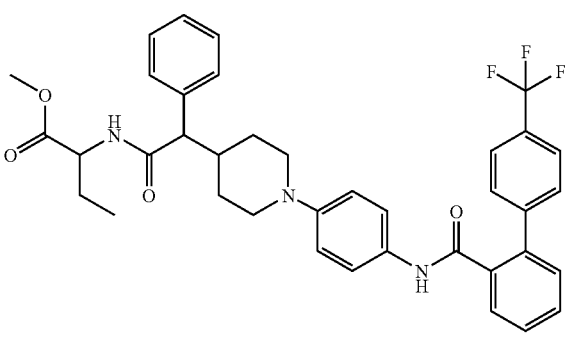
Co. No. 103; Ex. B.7
TABLE F-1-continued
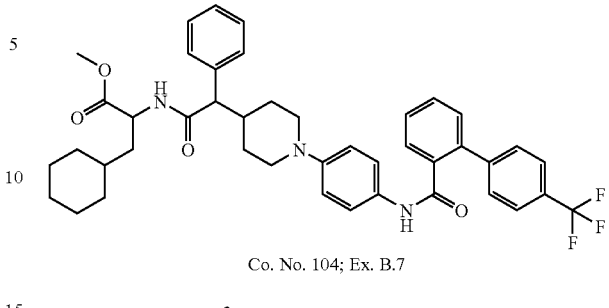
Co. No. 104; Ex. B.7
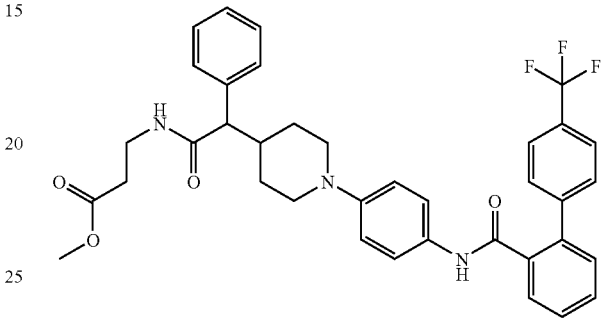
Co. No. 105; Ex. B.7
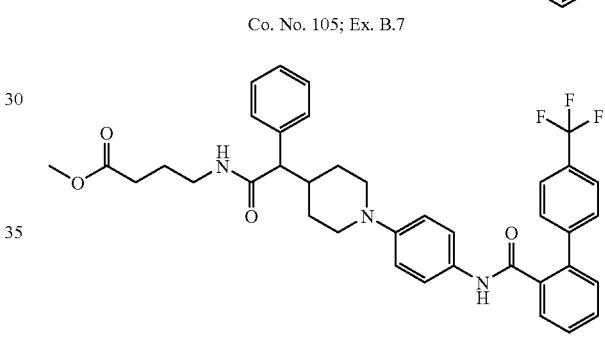
Co. No. 106; Ex. B.7
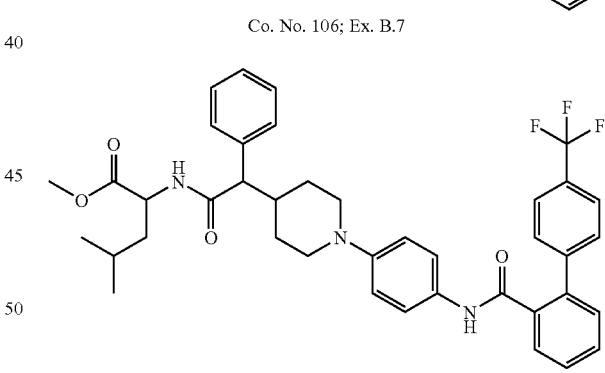
(S); Co. No. 107; Ex. B.7
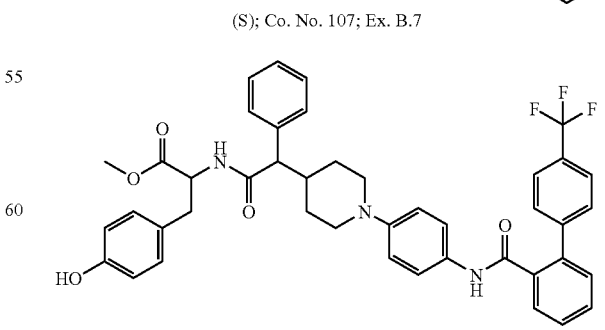
(S); Co. No. 108; Ex. B.7

TABLE F-1-continued
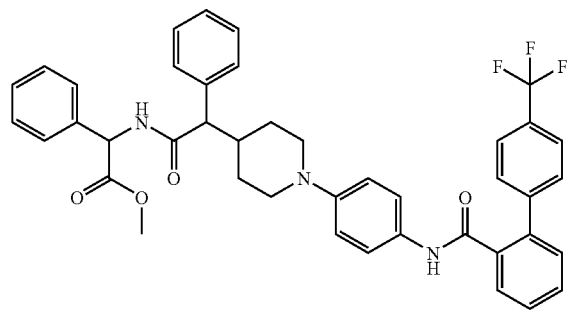
(R); Co. No. 109; Ex. B.7
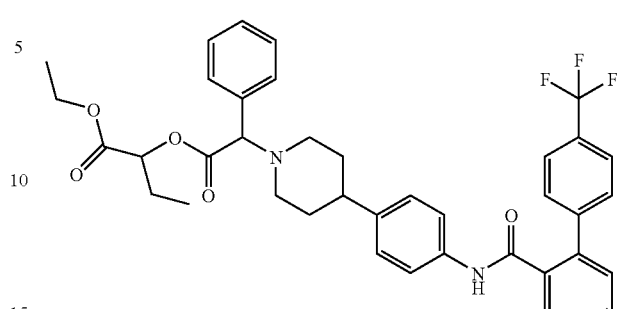
Co. No. 113; Ex. B.8
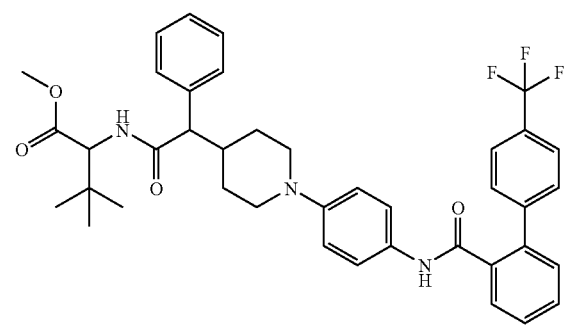
(S); Co. No. 110; Ex. B.7
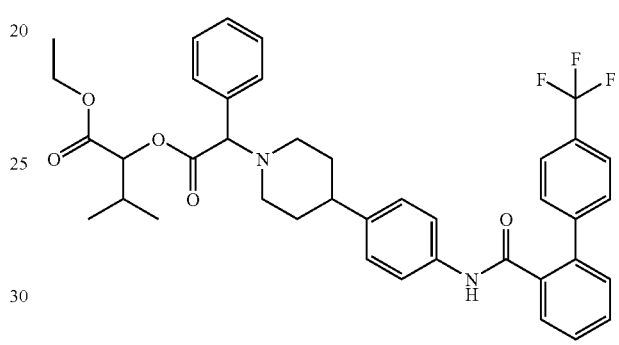
Co. No. 114; Ex. B.8
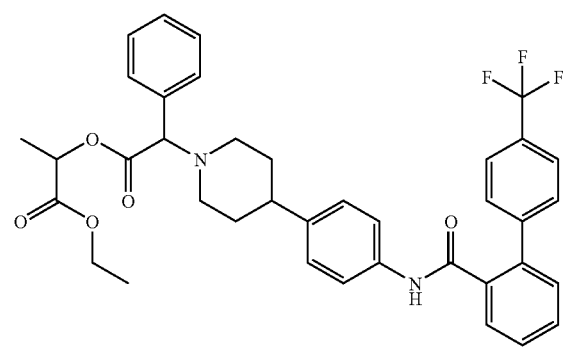
Co. No. 111; Ex. B.8
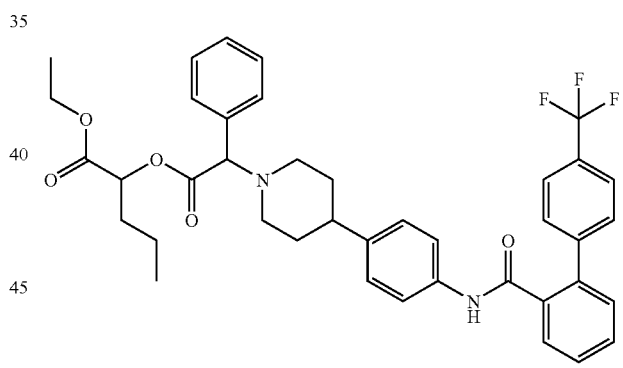
Co. No. 115; Ex. B.8
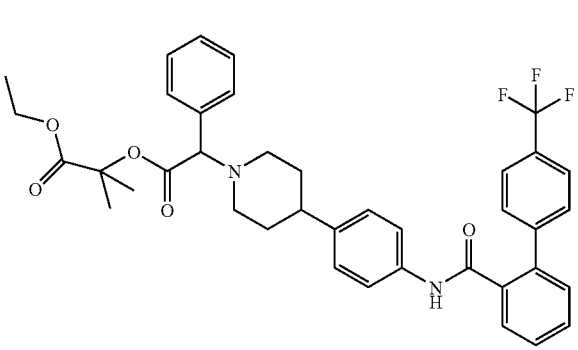
Co. No. 112; Ex. B.8
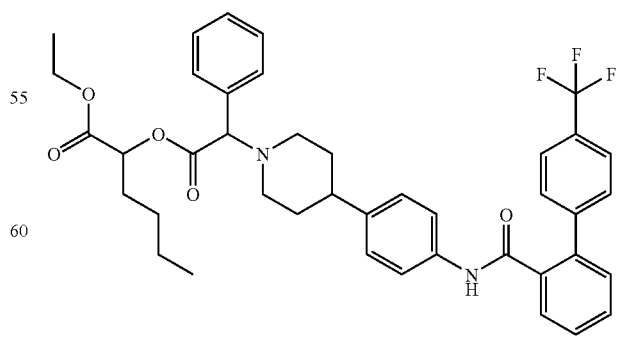
Co. No. 116; Ex. B.8

TABLE F-1-continued
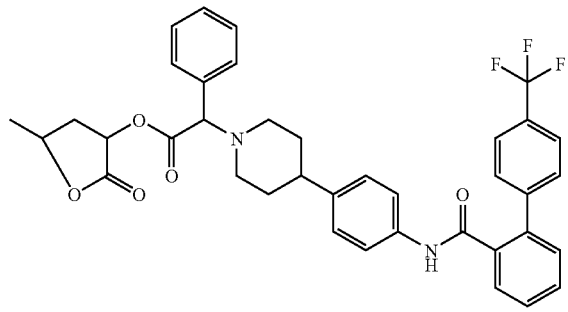
Co. No. 117; Ex. B.8
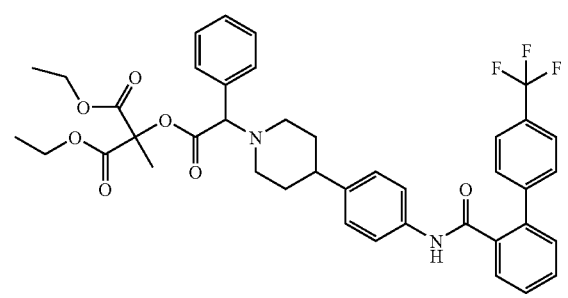
Co. No. 118; Ex. B.8
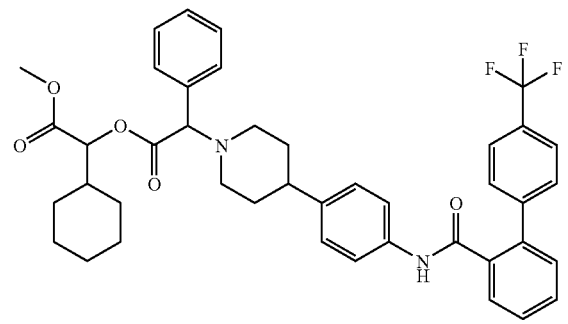
Co. No. 119; Ex. B.8
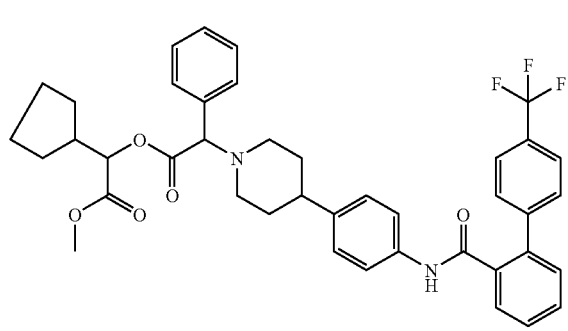
Co. No. 120; Ex. B.8
TABLE F-1-continued
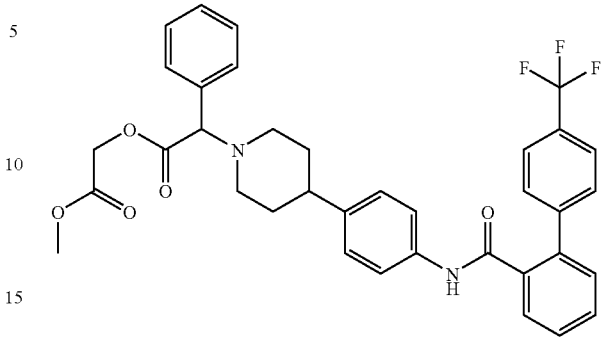
Co. No. 121; Ex. B.8
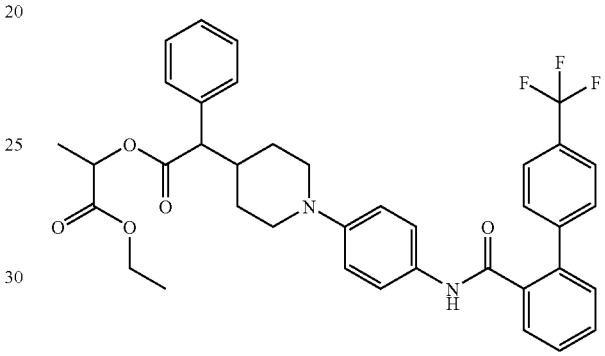
Co. No. 122; Ex. B.8
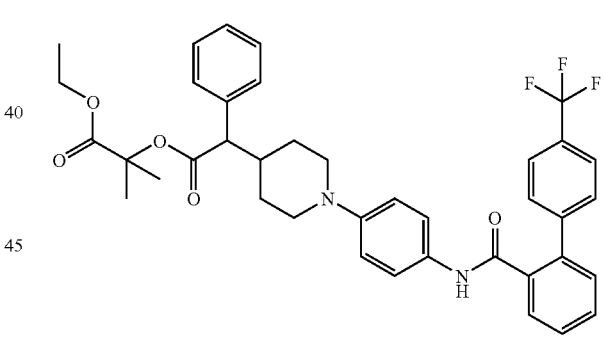
Co. No. 123; Ex. B.8
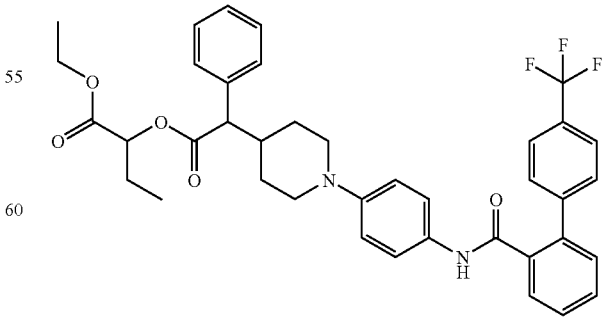
Co. No. 124; Ex. B.8

TABLE F-1-continued
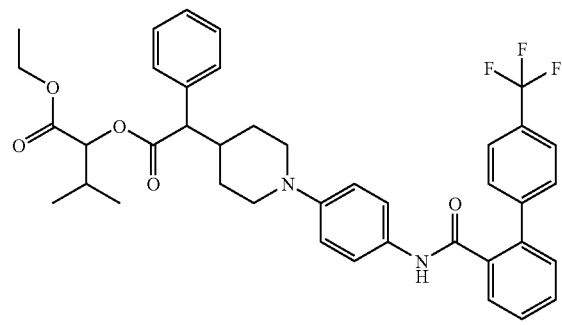
Co. No. 125; Ex. B.8
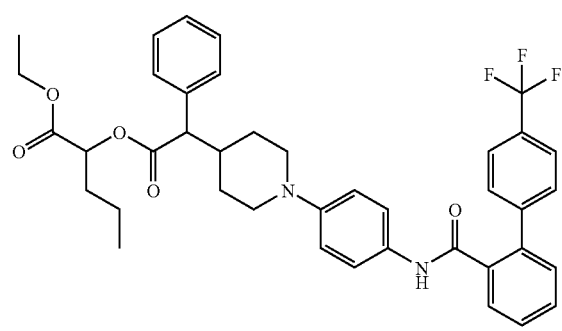
Co. No. 126; Ex. B.8
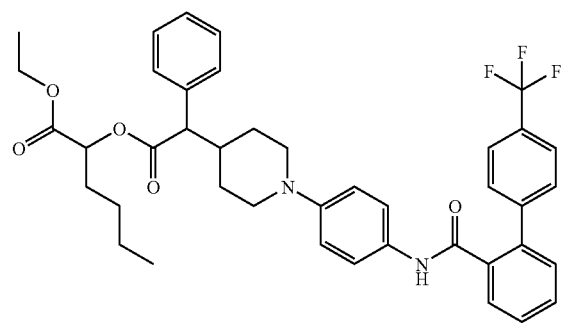
Co. No. 127; Ex. B.8
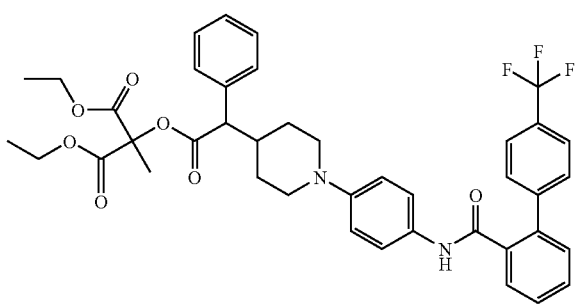
Co. No. 128; Ex. B.8
TABLE F-1-continued
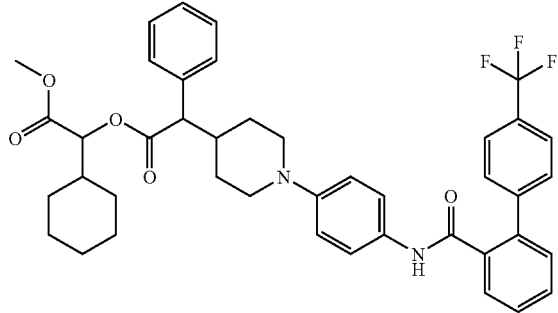
Co. No. 129; Ex. B.8
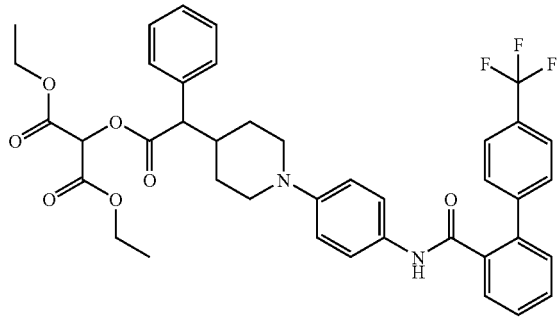
Co. No. 130; Ex. B.8
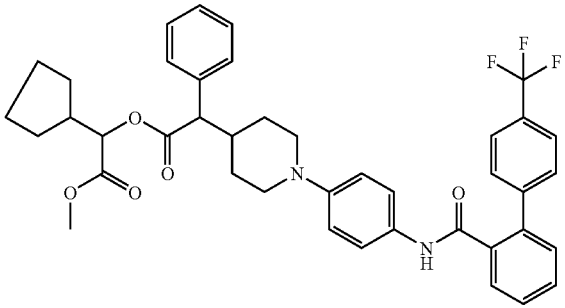
Co. No. 131; Ex. B.8
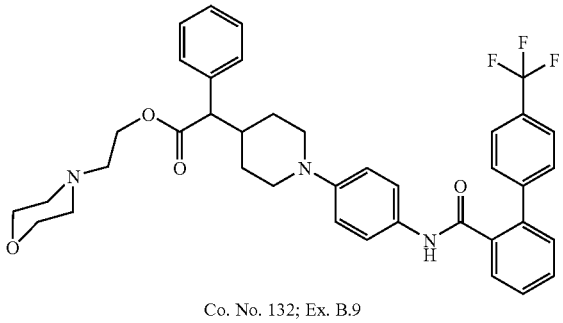
Co. No. 132; Ex. B.9
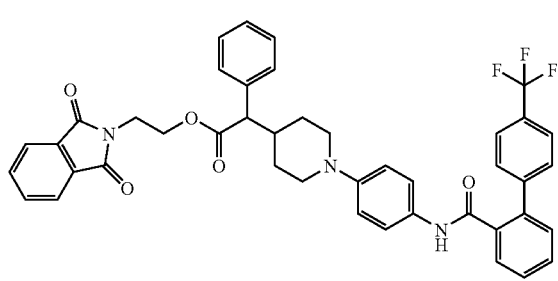
Co. No. 133; Ex. B.9

TABLE F-1-continued
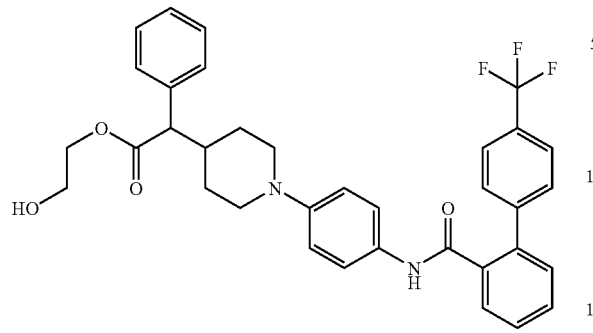
Co. No. 134; Ex. B.9
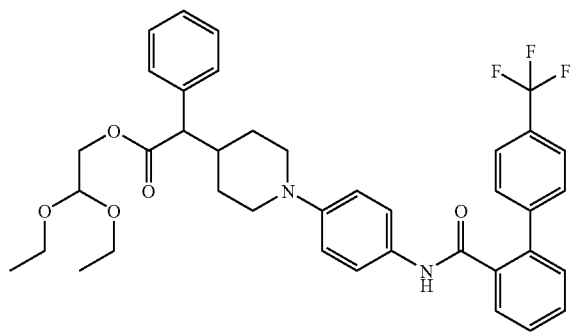
Co. No. 135; Ex. B.9
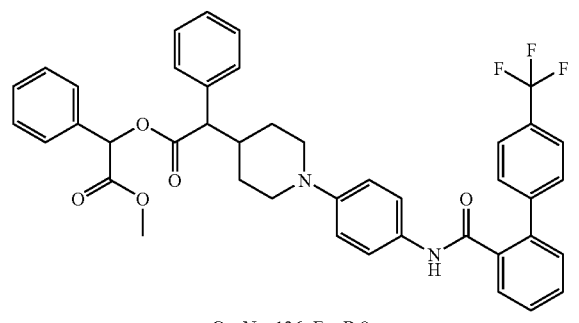
Co. No. 136; Ex. B.9
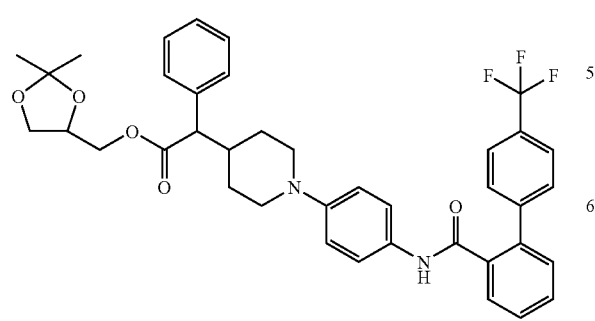
Co. No. 137; Ex. B.9
TABLE F-1-continued
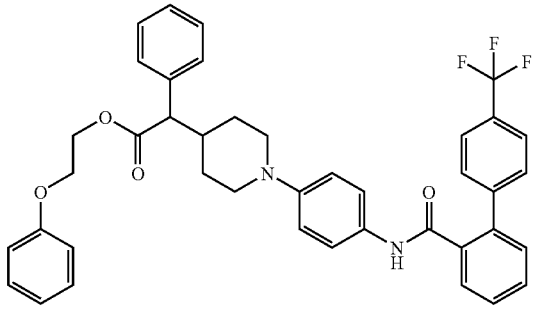
Co. No. 138; Ex. B.9
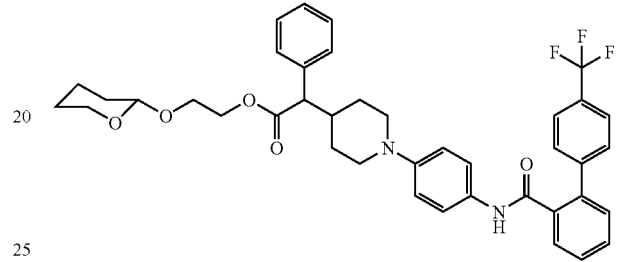
Co. No. 139; Ex. B.9
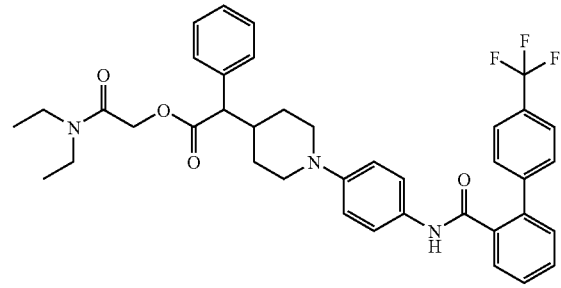
Co. No. 140; Ex. B.9
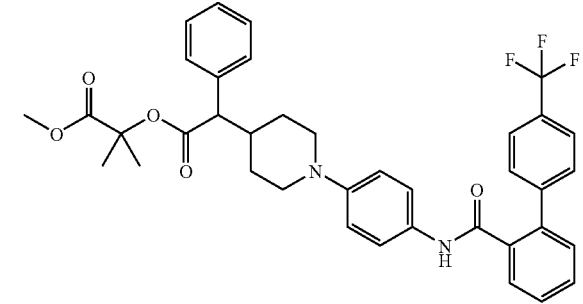
Co. No. 141; Ex. B.9
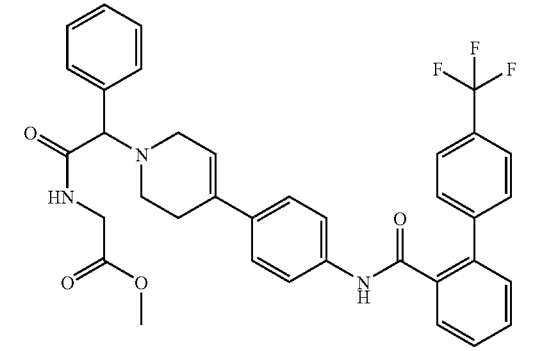
Co. No. 142; Ex. B.10

TABLE F-1-continued

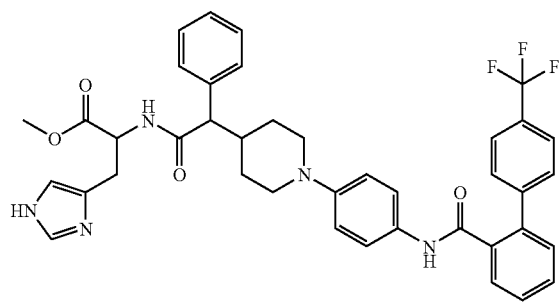

Co. No. 143; Ex. B.12

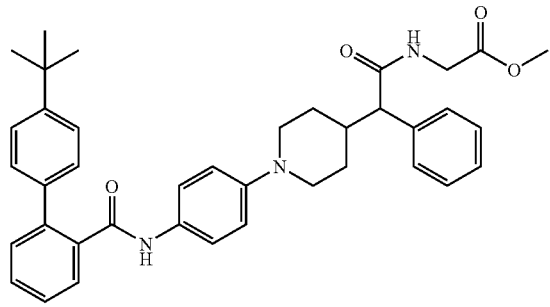

Co. No. 144; Ex. B.13;
mp. 119.7-119.8° C.; $[\alpha]_D^{20} = -25.99°$
(c = 24.05 mg/5 ml in DMF)

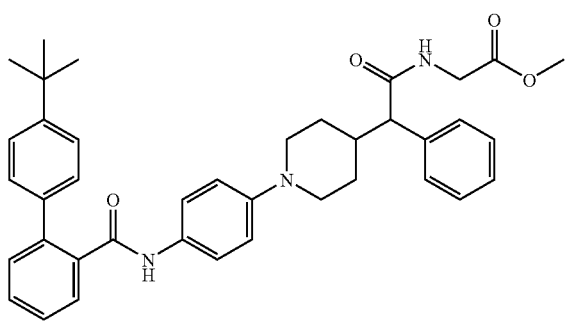

Co. No. 145; Ex. B.13;
mp. 119.9-120° C.; $[\alpha]_D^{20} = 28.78°$
(c = 25.19 mg/5 ml in DMF)

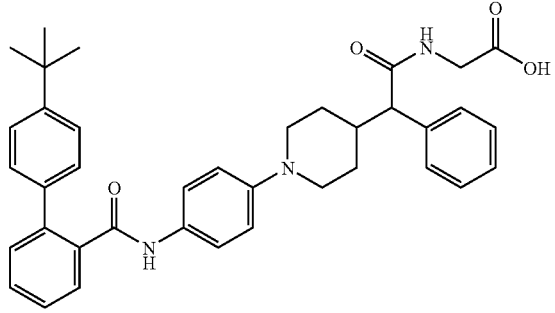

Co. No. 146; Ex. B.3; •HCl•H$_2$O;
mp. 245.-245.3° C.; $[\alpha]_D^{20} = -8.73°$
(c = 25.19 mg/5 ml in DMF)

TABLE F-1-continued

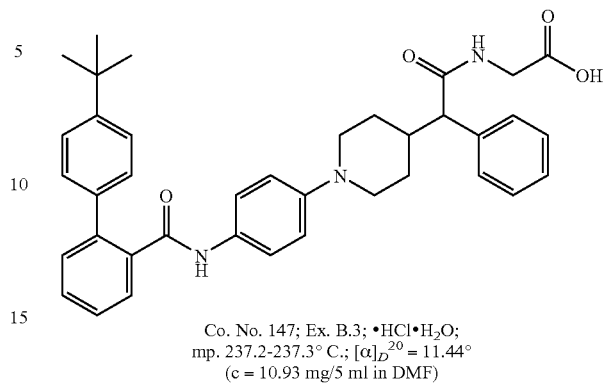

Co. No. 147; Ex. B.3; •HCl•H$_2$O;
mp. 237.2-237.3° C.; $[\alpha]_D^{20} = 11.44°$
(c = 10.93 mg/5 ml in DMF)

C. Pharmacological Examples.

C. 1. Quantification of the Secretion of ApoB.

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM NaH$_2$PO$_4$, 100 mM NaF, 0.2 mM DTT, 5 mM EDTA, 5 mM EGTA, 1% Triton-X-100, 0.5% sodium deoxycholate (DOC), 0.1% SDS, 0.2 µM leupeptin and 0.2 µM PMSF. Radioactivity in the pellet was quantified by liquid scintillation counting.

Resulting IC$_{50}$ values are enumerated in Table C. 1.

TABLE C.1

| Co. No. | pIC50 values (=−log IC$_{50}$ value) pIC50 |
|---|---|
| 1 | 7.153 |
| 2 | 5.767 |
| 3 | 8.125 |
| 4 | 6.842 |
| 5 | 5.635 |
| 6 | >7.523 |
| 7 | >7.523 |
| 8 | 5.892 |
| 9 | 5.938 |
| 10 | 7.231 |
| 11 | 6.059 |
| 12 | 7.651 |
| 13 | 5.991 |
| 14 | 6.591 |
| 15 | 6.641 |
| 16 | 5.523 |
| 17 | 5.856 |
| 18 | 8.08 |
| 20 | 6.96 |
| 21 | 5.862 |
| 22 | 8.458 |
| 23 | 5.523 |
| 24 | 5.603 |
| 25 | 6.887 |
| 26 | 6.64 |

TABLE C.1-continued

| Co. No. | pIC50 (=−log IC50 value) |
|---|---|
| 27 | 6.696 |
| 28 | 6.226 |
| 29 | 7.368 |
| 30 | 7.041 |
| 31 | 6.974 |
| 32 | 7.138 |
| 33 | >7.523 |
| 34 | 5.912 |
| 35 | 6.951 |
| 36 | >7.523 |
| 37 | 7.174 |
| 38 | 7.047 |
| 39 | >7.523 |
| 40 | >7.523 |
| 41 | 6.536 |
| 42 | 6.233 |
| 43 | 5.861 |
| 44 | >7.523 |
| 45 | 6.597 |
| 46 | 7.136 |
| 47 | 6.763 |
| 48 | 6.338 |
| 49 | 7.19 |
| 50 | 6.58 |
| 51 | 6.614 |
| 52 | 6.793 |
| 53 | >7.523 |
| 59 | 5.996 |
| 60 | 5.523 |
| 62 | >7.523 |
| 63 | 5.523 |
| 66 | 5.523 |
| 67 | 5.523 |
| 68 | 6.215 |
| 69 | 5.767 |
| 70 | 5.523 |
| 71 | 5.523 |
| 72 | >7.523 |
| 73 | 6.776 |
| 76 | 6.443 |
| 77 | 6.07 |
| 78 | 7.1 |
| 90 | >7.523 |
| 91 | 7.47 |
| 92 | 7.371 |
| 93 | 7.492 |
| 94 | 6.137 |
| 95 | 6.575 |
| 96 | 5.787 |
| 97 | 6.856 |
| 98 | 6.233 |
| 99 | 6.035 |
| 108 | 5.523 |

C.2. MTP Assay

MTP activity was measured using an assay similar to one described by J. R. Wetterau and D. B. Zilversmit in *Chemistry and Physics of Lipids*, 38, 205-222 (1985). To prepare the donor and acceptor vesicles, the appropriate lipids in chloroform were put into a glass test tube and dried under a stream of $N_2$. A buffer containing 15 mM Tris-HCl pH 7.5, 1 mM EDTA, 40 mM NaCl, 0.02% $NaN_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri[1-$^{14}$C]-oleate), acceptor vesicles (240 nmol phosphatidylcholine) and 5 mg BSA in a total volume of 675 µl in a 1.5 ml microcentrifuge tube. Test compounds were added dissolved in DMSO (0.13% final concentration). After 5 minutes of pre-incubation at 37° C., the reaction was started by the addition of MTP in 100 µl dialysis buffer. The reaction was stopped by the addition of 400 µl DEAE-52 cellulose pre-equilibrated in 15 mM Tris-HCl pH 7.5, 1 mM EDTA, 0.02% $NaN_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

The invention claimed is:

1. A compound of formula (I)

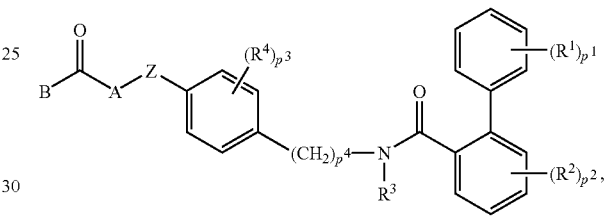

the N-oxides, the pharmaceutically acceptable acid addition salts and the stereochemically isomeric forms thereof, wherein $p^1$, $p^2$ and $p^3$ are integers each independently from 1 to 3;

$p^4$ is an integer zero or 1;

each $R^1$ is independently selected from hydrogen, $C_{1-4}$alkyl, $C_{1-4}$alkyloxy, halo, hydroxy, mercapto, cyano, nitro, $C_{1-4}$alkylthio or polyhalo$C_{1-6}$alkyl, amino, $C_{1-4}$alkylamino and di($C_{1-4}$alkyl)amino;

each $R^2$ is independently selected from hydrogen, $C_{1-4}$alkyl, $C_{1-4}$alkyloxy, halo, or trifluoromethyl;

$R^3$ is hydrogen or $C_{1-4}$alkyl;

each $R^4$ is independently selected from hydrogen, $C_{1-4}$alkyl, $C_{1-4}$alkyloxy, halo, or trifluoromethyl;

Z is a bivalent radical of formula

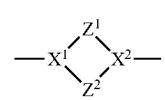

(a-5)

wherein $X^1$ and $X^2$ are each independently selected from CH, N or an sp$^2$ hybridized carbon atom;

$Z^1$ is selected from $CH_2$, $CH_2CH_2$, $CH_2CH_2CH_2$, $CH_2CH_2O$ and $OCH_2CH_2$;

$Z^2$ is $CH_2$ or $CH_2CH_2$;

A represents $C_{1-6}$alkanediyl substituted with one or two groups selected from aryl, heteroaryl and $C_{3-6}$cycloalkyl;

B represents a radical of formula
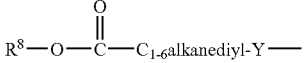 (b-1)
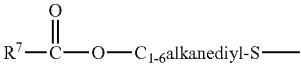 (b-2)
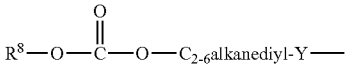 (b-3)
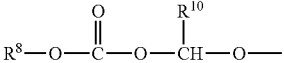 (b-4)
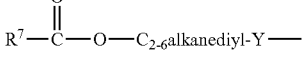 (b-5)
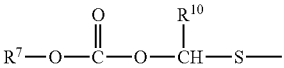 (b-6)
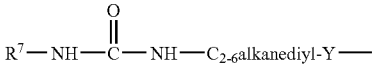 (b-7)
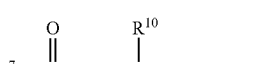 (b-8)
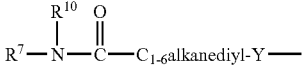 (b-9)
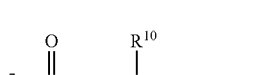 (b-10)
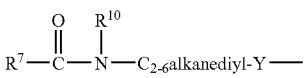 (b-11)
$R^7$—O—$C_{1-6}$alkanediyl-Y— (b-12)
$R^7$—S—$C_{1-6}$alkanediyl-Y— (b-13)
NC—$C_{1-6}$alkanediyl-Y— (b-14)
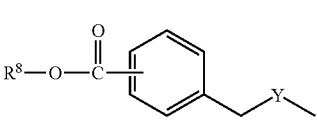 (b-15)
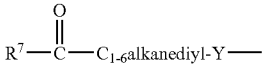 (b-16)
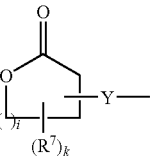 (b-17)
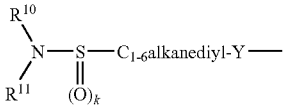 (b-18)
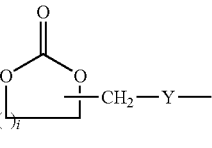 (b-19)
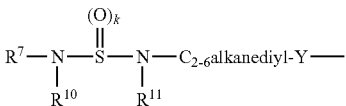 (b-20)
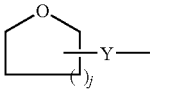 (b-21)
 (b-22)
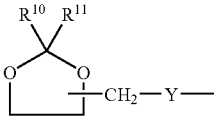 (b-23)
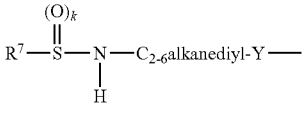 (b-24)
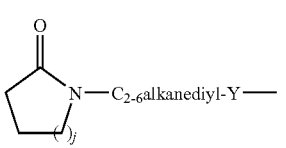 (b-25)
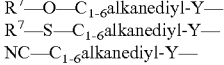 (b-26)
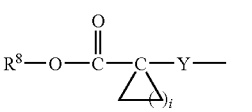 (b-27)
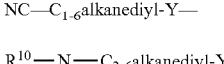 (b-28)
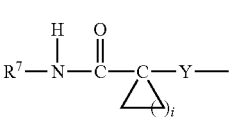 (b-29)
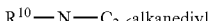 (b-30)
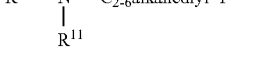 (b-31)

-continued

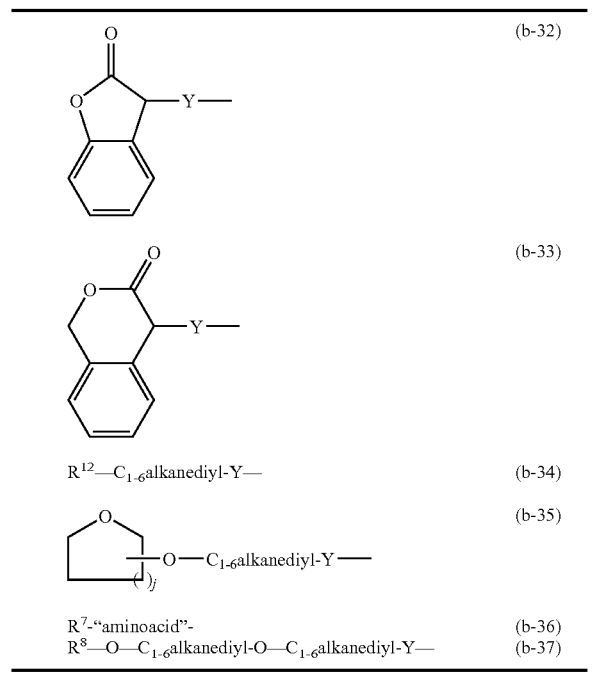

| | |
|---|---|
| | (b-32) |
| | (b-33) |
| R¹²—C₁₋₆alkanediyl-Y— | (b-34) |
| | (b-35) |
| R⁷-"aminoacid"- | (b-36) |
| R⁸—O—C₁₋₆alkanediyl-O—C₁₋₆alkanediyl-Y— | (b-37) | wherein i is an integer 1 to 4;
  j is an integer 1 to 4;
  k is an integer 1 or 2;
  Y is O or NR⁹ wherein R⁹ is hydrogen, C₁₋₆alkyl or C₁₋₄alkylaminocarbonyl;
  R⁷ is hydrogen, C₁₋₆alkyl, C₂₋₆alkenyl, C₂₋₆alkynyl, phenyl, or phenyl substituted with C₁₋₄alkyl, halo, hydroxy or trifluoromethyl;
  R⁸ is C₁₋₆alkyl, C₂₋₆alkenyl, C₂₋₆alkynyl, phenyl, or phenyl substituted with C₁₋₄alkyl, halo, hydroxy or trifluoromethyl;
  R¹⁰ and R¹¹ are each independently hydrogen or C₁₋₆alkyl;
  optionally R⁷ and R⁹ can be taken together to form a bivalent radical of formula —(CH₂)₃—, —(CH₂)₄—, —(CH₂)₅—, or —(CH₂)₆—;
  R¹² is a radical of formula

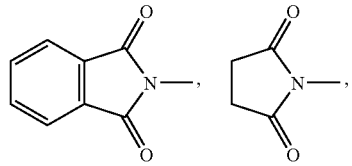

-continued

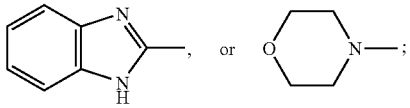

the amino acid is selected from the group consisting of glycine, alanine, valine, leucine, isoleucine, methionine, proline, phenylanaline, tryptophan, serine, threonine, cysteine, tyrosine, asparagine, glutamine, aspartic acid, esters of aspartic acid, glutamic acid, esters of glutamic acid, lysine, arginine, and histidine; and optionally in radical (b-1) the C₁₋₆alkanediyl moiety can be further substituted with phenyl, phenylC₁₋₄alkyl, hydroxyphenylC₁₋₄alkyl, C₁₋₄alkyloxycarbonyl, C₁₋₄alkyloxyC₁₋₄alkyl, C₁₋₄alkylthioC₁₋₄alkyl, phenylC₁₋₄alkylthioC₁₋₄alkyl, hydroxyC₁₋₄alkyl, thioC₁₋₄alkyl, C₃₋₆cycloalkyl, C₃₋₆cycloalkylC₁₋₄alkyl, or a radical of formula

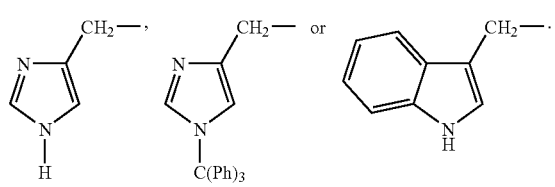

2. A compound as claimed in claim 1 wherein R¹ is hydrogen, tert-butyl or trifluoromethyl; R², R³ and R⁴ are hydrogen.

3. A compound as claimed in claim 1 wherein the bivalent radical A represents a methylene group substituted with phenyl.

4. A compound as claimed in claim 1 wherein Z is a bivalent radical of formula (a-5) wherein Z¹ and Z² represent CH₂CH₂ and X¹ is N and X² is CH.

5. A compound as claimed in claim 1 wherein Z is a bivalent radical of formula (a-5) wherein Z¹ and Z² represent CH₂CH₂ and X¹ is CH and X² is N.

6. A compound as claimed in claim 1 wherein Z is a bivalent radical of formula (a-5) wherein Z¹ and Z² represent CH₂CH₂ and X¹ and X² are N.

7. A pharmaceutical composition comprising a pharmaceutically acceptable carrier and a therapeutically active amount of a compound as claimed in claim 1.

\* \* \* \* \*